(12) United States Patent
McCallus et al.

(10) Patent No.: US 8,987,227 B2
(45) Date of Patent: Mar. 24, 2015

(54) HEPATITIS C DSRNA EFFECTOR MOLECULES, EXPRESSION CONSTRUCTS, COMPOSITIONS, AND METHODS OF USE

(71) Applicant: Alnylam Pharmaceuticals, Inc., Cambridge, MA (US)

(72) Inventors: Daniel McCallus, Cambridge, MA (US); Catherine Pachuk, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/080,342

(22) Filed: Nov. 14, 2013

(65) Prior Publication Data
US 2014/0141512 A1    May 22, 2014

Related U.S. Application Data

(63) Continuation of application No. 12/666,057, filed as application No. PCT/US2008/067871 on Jun. 23, 2008, now Pat. No. 8,614,198.

(60) Provisional application No. 60/929,335, filed on Jun. 22, 2007.

(51) Int. Cl.
*A61K 48/00* (2006.01)
*C12N 15/11* (2006.01)
*C07H 21/02* (2006.01)
*C07H 21/04* (2006.01)
*C12N 15/113* (2010.01)

(52) U.S. Cl.
CPC ...... *C12N 15/1131* (2013.01); *C12N 2310/111* (2013.01); *C12N 2310/14* (2013.01); *C12N 2310/53* (2013.01)
USPC ........................................ 514/44 A; 536/24.5

(58) Field of Classification Search
USPC ........................................... 514/44; 536/24.5
See application file for complete search history.

(56) References Cited

U.S. PATENT DOCUMENTS 8,614,198 B2 * 12/2013 McCallus et al. ........... 514/44 A
2005/0197313 A1    9/2005 Roelvink et al.

FOREIGN PATENT DOCUMENTS

| WO | 2005/028650 A2 | 3/2005 |
| WO | 2006/036872 A2 | 4/2006 |
| WO | 2006/084209 A2 | 8/2006 |

*Primary Examiner* — Terra Cotta Gibbs
(74) *Attorney, Agent, or Firm* — Nixon Peabody LLP; Mark J. FitzGerald

(57) ABSTRACT

The present invention provides agents, compositions, constructs and methods for silencing HCV polynucleotides, as well as methods and compositions for treating or preventing HCV infection in a mammalian cell. In one aspect, the present invention provides an agent or composition comprising at least one double-stranded RNA effector molecule or complex. The double-stranded RNA effector molecule or complex comprises: (1) a sequence of at least 19 nucleotides having at least 90% identity with a nucleotide sequence within HCV Conserved Region 1 (SEQ ID NO: 2), HCV Conserved Region 2 (SEQ ID NO: 3), HCV Conserved Region 5 (SEQ ID NO: 4), (ATR)-1 (SEQ ID NO: 86), ATR-2 (SEQ ID NO: 87), ATR-3 (SEQ ID NO: 88), ATR-4 (SEQ ID NO: 89); and (2) its complementary sequence. In another aspect, the present invention provides a construct suitable for replication in a host cell, and/or suitable for expression of an RNA molecule or complex of the invention in vitro or in vivo. In a third aspect, the present invention provides a method for silencing HCV RNA in a mammalian cell, which comprises administering to the mammalian cell an agent, composition, or construct of the invention in a manner and amount effective to silence HCV RNA in the cell. In a related aspect, the invention provides a method for treating or preventing HCV infection in a patient, comprising administering to the patient an effective amount of an agent, composition, or construct of the invention as described herein.

7 Claims, 3 Drawing Sheets

SEQUENCE LISTING

<160> NUMBER OF SEQ ID NOS: 89

<210> SEQ ID NO 1
<211> LENGTH: 9678
<212> TYPE: DNA
<213> ORGANISM: Hepatitis C virus

<400> SEQUENCE: 1

```
acctgcccct aatagggggcg acactccgcc atgaatcact ccctgtgag gaactactgt      60 cttcacgcag aaagcgccta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttggggttg cgaaaggcct tgtggtactg cctgataggg     300
```

```
cgcttgcgag tgccccggga ggtctcgtag accgtgcacc atgagcacaa atcctaaacc    360
tcaaagaaaa accaaaagaa acaccaaccg tcgcccagaa gacgttaagt tcccgggcgg    420
cggccagatc gttggcggag tatacttgtt gccgcgcagg ggcccaggt tgggtgtgcg    480 cacgacaagg aaaacttcgg agcggtccca gccacgtggg agacgccagc ccatccccaa    540
agatcggcgc tccactggca aggcctgggg aaaaccaggt cgccctggc ccctatatgg    600 gaatgaggga ctcggctggg caggatggct cctgtcccc cgaggctctc gccctcctg    660 gggccccact gaccccggc ataggtcgcg caacgtgggt aaagtcatcg acaccctaac    720
gtgtggcttt gccgacctca tggggtacat ccccgtcgta ggcgccccgc ttagtggcgc    780
cgccagagct gtcgcgcacg gcgtgagagt cctggaggac ggggttaatt atgcaacagg    840
gaacctaccc ggtttcccct tttctatctt cttgctggcc ctgttgtcct gcatcaccgt    900
tccggtctct gctgcccagg tgaagaatac cagtagcagc tacatggtga ccaatgactg    960
ctccaatgac agcatcactt ggcagctcga ggctgcggtt ctccacgtcc ccgggtgcgt   1020
cccgtgcgag agagtgggga atacgtcacg gtgttgggtg ccagtctcgc caaacatggc   1080
tgtgcggcag cccggtgccc tcacgcaggg tctgcggacg cacatcgata tggttgtgat   1140
gtccgccacc ttctgctctg ctctctacgt gggggacctc tgtggcgggg tgatgctcgc   1200
ggcccaggtg ttcatcgtct cgccgcagta ccactggttt gtgcaagaat gcaattgctc   1260
catctaccct ggcaccatca ctggacaccg catggcatgg acatgatga tgaactggtc    1320 gcccacggcc accatgatcc tggcgtacgt gatgcgcgtc cccgaggtca tcatagacat   1380
cgttagcggg gctcactggg gcgtcatgtt cggcttggcc tacttctcta tgcagggagc   1440
gtgggcgaag gtcattgtca tccttctgct ggccgctggg gtggacgcgg gcaccaccac   1500
cgttggaggc gctgttgcac gttccaccaa cgtgattgcc ggcgtgttca gccatggccc   1560
tcagcagaac attcagctca ttaacaccaa cggcagttgg cacatcaacc gtactgcctt   1620
gaattgcaat gactccttga acaccggctt tctcgcggcc ttgttctaca ccaaccgctt   1680
taactcgtca gggtgtccag ggcgcctgtc cgcctgccgc aacatcgagg ctttccggat   1740
agggtggggc accctacagt acgaggataa tgtcaccaat ccagaggata tgaggccgta   1800
ctgctggcac tacccccaa agccgtgtgg cgtagtcccc gcgaggtctg tgtgtggccc    1860
agtgtactgt ttcaccccca gcccggtagt agtgggcacg accgacagac gtggagtgcc   1920
cacctacaca tggggagaga atgagacaga tgtcttccta ctgaacagca cccgaccgcc   1980
gcagggctca tggttcggct gcacgtggat gaactccact ggtttcacca agacttgtgg   2040
cgcgccacct tgccgcacca gagctgactt caacgccagc acggacttgt tgtgccctac   2100
ggattgtttt aggaagcatc ctgatgccac ttatattaag tgtggttctg ggccctggct   2160
cacaccaaag tgcctggtcc actacccta cagactctgg cattacccct gcacagtcaa   2220
ttttaccatc ttcaagataa gaatgtatgt aggggggtt gagcacaggc tcacggccgc   2280
atgcaacttc actcgtgggg atcgctgcga cttggaggac agggacagga gtcagctgtc   2340
tcctctgttg cactctacca cggaatgggc catcctgccc tgcacctact cagacttacc   2400
cgctttgtca actggtcttc tccaccttca ccagaacatc gtggacgtac aatacatgta   2460
tggcctctca cctgctatca caaaatacgt cgttcgatgg gagtgggtgg tactcttatt   2520
cctgctctta gcgacgcca gagtctcgc ctgcttgtgg atgctcatct tgttgggcca    2580
ggccgaagca gcattggaga agttggtcgt cttgcacgct gcgagtgcgg ctaactgcca   2640
```

```
tggcctccta tattttgcca tcttcttcgt ggcagcttgg cacatcaggg gtcgggtggt      2700 cccttgacc acctattgcc tcactggcct atggcccttc tgcctactgc tcatggcact       2760
gccccggcag gcttatgcct atgacgcacc tgtgcacgga cagataggcg tgggtttgtt      2820
gatattgatc accctcttca cactcacccc ggggtataag accctcctcg gccagtgtct      2880
gtggtggttg tgctatctcc tgaccctggg ggaagccatg attcaggagt gggtaccacc      2940
catgcaggtg cgcggcggcc gcgatggcat cgcgtgggcc gtcactatat tctgcccggg      3000
tgtggtgttt gacattacca aatggctttt ggcgttgctt gggcctgctt acctcttaag      3060
ggccgctttg acacatgtgc cgtacttcgt cagagctcac gctctgataa gggtatgcgc      3120
tttggtgaag cagctcgcgg ggggtaggta tgttcaggtg gcgctattgg cccttggcag      3180
gtggactggc acctacatct atgaccacct cacacctatg tcggactggg ccgctagcgg      3240
cctgcgcgac ttagcggtcg ccgtggaacc catcatcttc agtccgatgg agaagaaggt      3300
catcgtctgg ggagcggaga cggctgcatg tggggacatt ctacatggac ttcccgtgtc      3360
cgcccgactc ggccaggaga tcctcctcgg cccagctgat ggctacacct ccaagggggtg     3420 gaagctcctt gctcccatca ctgcttatgc ccagcaaaca cgaggcctcc tgggcgccat      3480
agtggtgagt atgacggggc gtgacaggac agaacaggcc ggggaagtcc aaatcctgtc      3540
cacagtctct cagtccttcc tcggaacaac catctcgggg gttttgtgga ctgtttacca      3600
cggagctggc aacaagactc tagccggctt acggggtccg gtcacgcaga tgtactcgag      3660
tgctgagggg gacttggtag gctggcccag ccccctggg accaagtctt tggagccgtg       3720
caagtgtgga gccgtcgacc tatatctggt cacgcggaac gctgatgtca tcccggctcg      3780
gagacgcggg gacaagcggg gagcattgct ctccccgaga cccatttcga ccttgaaggg      3840
gtcctcgggg gggccggtgc tctgcccctag gggccacgtc gttgggctct ccgagcagc     3900 tgtgtgctct cggggcgtgg ccaaatccat cgatttcatc cccgttgaga cactcgacgt      3960
tgttacaagg tctcccactt tcagtgacaa cagcacgcca ccggctgtgc cccagaccta      4020
tcaggtcggg tacttgcatg ctccaactgg cagtggaaag agcaccaagg tccctgtcgc      4080
gtatgccgcc caggggtaca aagtactagt gcttaaccc tcggtagctg ccaccctggg      4140
gtttggggcg tacctatcca aggcacatgg catcaatccc aacattagga ctggagtcag      4200
gaccgtgatg accggggagg ccatcacgta ctccacatat ggcaaatttc tcgccgatgg      4260
gggctgcgct agcggcgcct atgacatcat catatgcgat gaatgccacg ctgtggatgc      4320
tacctccatt ctcggcatcg gaacggtcct tgatcaagca gagacagccg gggtcagact      4380
aactgtgctg gctacggcca caccccccgg gtcagtgaca acccccccatc ccgatataga    4440 agaggtaggc ctcgggcggg agggtgagat ccccttctat gggagggcga ttccctatc      4500 ctgcatcaag ggagggagac acctgatttt ctgccactca aagaaaaagt gtgacgagct      4560
cgcggcggcc cttcggggca tgggcttgaa tgccgtggca tactatagag ggttggacgt      4620
ctccataata ccagctcagg gagatgtggt ggtcgtcgcc accgacgccc tcatgacggg      4680
gtacactgga gactttgact ccgtgatcga ctgcaatgta gcggtcaccc aagctgtcga     4740
cttcagcctg gaccccacct tcactataac cacacagact gtcccacaag acgctgtctc     4800
acgcagtcag cgccgcgggc gcacaggtag aggaagacag ggcacttata ggtatgtttc     4860
cactggtgaa cgagcctcag gaatgtttga cagtgtagtg ctttgtgagt gctacgacgc     4920
aggggctgcg tggtacgatc tcacaccagc ggagaccacc gtcaggctta gagcgtattt     4980
caacacgccc ggcctacccg tgtgtcaaga ccatcttgaa ttttgggagg cagttttcac     5040
```

```
cggcctcaca cacatagacg cccacttcct ctcccaaaca aagcaagcgg gggagaactt      5100
cgcgtaccta gtagcctacc aagctacggt gtgcgccaga gccaaggccc ctcccccgtc      5160
ctgggacgcc atgtggaagt gcctggcccg actcaagcct acgcttgcgg gccccacacc      5220
tctcctgtac cgtttgggcc ctattaccaa tgaggtcacc ctcacacacc ctgggacgaa      5280
gtacatcgcc acatgcatgc aagctgacct tgaggtcatg accagcacgt gggtcctagc      5340
tggaggagtc ctggcagccg tcgccgcata ttgcctggcg actggatgcg tttccatcat      5400
cggccgcttg cacgtcaacc agcgagtcgt cgttgcgccg gataaggagg tcctgtatga      5460
ggcttttgat gagatggagg aatgcgcctc tagggcggct ctcatcgaag aggggcagcg      5520
gatagccgag atgttgaagt ccaagatcca aggcttgctg cagcaggcct ctaagcaggc      5580
ccaggacata caacccgcta tgcaggcttc atggcccaaa gtggaacaat tgggccag       5640 acacatgtgg aacttcatta gcggcatcca ataccgcgca ggattgtcaa cactgccagg      5700
gaaccccgcg gtggcttcca tgatggcatt cagtgccgcc ctcaccagtc cgttgtcgac      5760
cagtaccacc atccttctca acatcatggg aggctggtta gcgtcccaga tcgcaccacc      5820
cgcgggggcc accggctttg tcgtcagtgg cctggtgggg gctgccgtgg gcagcatagg      5880
cctgggtaag gtgctggtgg acatcctggc aggatatggt gcgggcattt cggggggcct      5940
cgtcgcattc aagatcatgt ctggcgagaa gccctctatg gaagatgtca tcaatctact      6000
gcctgggatc ctgtctccgg gagccctggt ggtgggggtc atctgcgcgg ccattctgcg      6060
ccgccacgtg ggaccggggg agggcgcggt ccaatggatg aacaggctta ttgcctttgc      6120
ttccagagga aaccacgtcg cccctactca ctacgtgacg gagtcggatg cgtcgcagcg      6180
tgtgacccaa ctacttggct ctcttactat aaccagccta tcagaagac tccacaattg      6240 gataactgag gactgcccca tcccatgctc cggatcctgg ctccgcgacg tgtgggactg      6300
ggtttgcacc atcttgacag acttcaaaaa ttggctgacc tctaaattgt tccccaagct      6360
gcccggcctc ccccttcatct cttgtcaaaa ggggtacaag ggtgtgtggg ccggcactgg      6420
catcatgacc acgcgctgcc cttgcggcgc aacatctct ggcaatgtcc gcctgggctc      6480
tatgaggatc acagggccta aaacctgcat gaacacctgg caggggacct ttcctatcaa      6540
ttgctacacg gagggccagt gcgcgccgaa acccccacg aactacaaga ccgccatctg      6600
gagggtggcg gcctcggagt acgcggaggt gacgcagcat gggtcgtact cctatgtaac      6660
aggactgacc actgacaatc tgaaaattcc ttgccaacta ccttctccag agttttctc      6720 ctgggtggac ggtgtgcaga tccataggtt tgcacccaca ccaaagccgt ttttccggga      6780
tgaggtctcg ttctgcgttg ggcttaattc ctatgctgtc gggtcccagc ttccctgtga      6840
acctgagccc gacgcagacg tattgaggtc catgctaaca gatccgcccc acatcacggc      6900
ggagactgcg gcgcggcgct ggcacggggg atcacctcca tctgaggcga gctcctcagt      6960
gagccagcta tcagcaccgt cgctgcgggc cacctgcacc acccacagca cacctatga      7020 cgtggacatg gtcgatgcca acctgctcat ggaggcggt gtggctcaga cagagcctga      7080
gtccaggggt cccgttctgg actttctcga gccaatggcc gaggaagaga gcgaccttga      7140
gccctcaata ccatcggagt gcatgctccc caggagcggg tttccacggg ccttaccggc      7200
ttgggcacgg cctgactaca acccgccgct cgtggaatcg tggaggaggc cagattacca      7260
accgcccacc gttgctggtt gtgctctccc ccccccaag aaggcccga cgcctccccc      7320 aaggagacgc cggacagtgg gtctgagcga gagcaccata tcagaagccc tccagcaact      7380
```

```
ggccatcaag acctttggcc agcccccctc gagcggtgat gcaggctcgt ccacgggggc    7440
gggcgccgcc gaatccggcg gtccgacgtc ccctggtgag ccggcccct cagagacagg     7500 ttccgcctcc tctatgcccc ccctcgaggg ggagcctgga gatccggacc tggagtctga    7560
tcaggtagag cttcaacctc cccccaggg gggggggta gctcccggtt cgggctcggg      7620
gtcttggtct acttgctccg aggaggacga taccaccgtg tgctgctcca tgtcatactc    7680
ctggaccggg gctctaataa ctccctgtag ccccgaagag gaaaagttgc caatcaaccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccaccca ttctgcaaga tccaagtatg gattcggggc     7980
caaggaggtc cgcagcttgt ccgggagggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg gcttccagta ctccctgcc caacgggtgg agtatctctt     8280
gaaagcatgg gcggaaaaga aggaccccat gggttttcg tatgataccc gatgcttcga     8340
ctcaaccgtc actgagagag acatcaggac cgaggagtcc atataccagg cctgctccct    8400
gcccgaggag gcccgcactg ccatacactc gctgactgag agactttacg taggagggcc    8460
catgttcaac agcaagggtc aaacctgcgg ttacagacgt tgccgcgcca gcggggtgct    8520
aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640
aagccagggg actgaggagg acgagcggaa cctgagagcc ttcacggagg ccatgaccag    8700
gtactctgcc cctcctggtg atcccccag accggaatat gacctggagc taataacatc      8760
ctgttcctca aatgtgtctg tggcgttggg cccgcgggc cgccgcagat actacctgac      8820
cagagaccca accactccac tcgcccgggc tgcctgggaa acagttagac actccctat       8880 caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tcctttggac cttccagcca taattgagag    9060
gttacacggg cttgacgcct tttctatgca cacatactct caccacgaac tgacgcgggt    9120
ggcttcagcc ctcagaaaac ttggggcgcc accctcagg gtgtggaaga gtcgggctcg    9180
cgcagtcagg gcgtccctca tctcccgtgg agggaaagcg gccgtttgcg gccgatatct    9240
cttcaattgg gcggtgaaga ccaagctcaa actcactcca ttgccggagg cgcgcctact    9300
ggacttatcc agttggttca ccgtcggcgc cggcggggc gacattttc acagcgtgtc       9360 gcgcgcccga ccccgctcat tactcttcgg cctactccta cttttcgtag ggtaggcct     9420 cttcctactc cccgctcggt agagcggcac acactaggta cactccatag ctaactgttc    9480
cttttttttt tttttttttt tttttttttt tttttttttt tttttctttt ttttttttc     9540 cctctttctt cccttctcat cttattctac tttctttctt ggtggctcca tcttagccct    9600
agtcacggct agctgtgaaa ggtccgtgag ccgcatgact gcagagagtg ccgtaactgg    9660
tctctctgca gatcatgt                                                   9678
```

<210> SEQ ID NO 2
<211> LENGTH: 68
<212> TYPE: DNA
<213> ORGANISM: Hepatitis C virus

<400> SEQUENCE: 2
atcactcccc tgtgaggaac tactgtcttc acgcagaaag cgcctagcca tggcgttagt    60
atgagtgt    68

<210> SEQ ID NO 3
<211> LENGTH: 58
<212> TYPE: DNA
<213> ORGANISM: Hepatitis C virus

<400> SEQUENCE: 3
ccccccctcc cgggagagcc atagtggtct gcggaaccgg tgagtacacc ggaattgc    58

<210> SEQ ID NO 4
<211> LENGTH: 69
<212> TYPE: DNA
<213> ORGANISM: Hepatitis C virus

<400> SEQUENCE: 4
gcgaaaggcc ttgtggtact gcctgatagg gcgcttgcga gtgccccggg aggtctcgta    60
gaccgtgca    69

<210> SEQ ID NO 5
<211> LENGTH: 21
<212> TYPE: DNA
<213> ORGANISM: Hepatitis C virus

<400> SEQUENCE: 5
tcactcccct gtgaggaact a    21

<210> SEQ ID NO 6
<211> LENGTH: 21
<212> TYPE: DNA
<213> ORGANISM: Hepatitis C virus

<400> SEQUENCE: 6
ggaactactg tcttcacgca g    21

<210> SEQ ID NO 7
<211> LENGTH: 21
<212> TYPE: DNA
<213> ORGANISM: Hepatitis C virus

<400> SEQUENCE: 7 cccctcccg ggagagccat a    21

<210> SEQ ID NO 8
<211> LENGTH: 21
<212> TYPE: DNA
<213> ORGANISM: Hepatitis C virus

<400> SEQUENCE: 8
tcccgggaga gccatagtgg t    21

<210> SEQ ID NO 9
<211> LENGTH: 21
<212> TYPE: DNA
<213> ORGANISM: Hepatitis C virus

<400> SEQUENCE: 9
cccgggagag ccatagtggt c                                              21

<210> SEQ ID NO 10
<211> LENGTH: 21
<212> TYPE: DNA
<213> ORGANISM: Hepatitis C virus

<400> SEQUENCE: 10
ccgggagagc catagtggtc t                                              21

<210> SEQ ID NO 11
<211> LENGTH: 21
<212> TYPE: DNA
<213> ORGANISM: Hepatitis C virus

<400> SEQUENCE: 11
gagagccata gtggtctgcg g                                              21

<210> SEQ ID NO 12
<211> LENGTH: 21
<212> TYPE: DNA
<213> ORGANISM: Hepatitis C virus

<400> SEQUENCE: 12
gagccatagt ggtctgcgga a                                              21

<210> SEQ ID NO 13
<211> LENGTH: 21
<212> TYPE: DNA
<213> ORGANISM: Hepatitis C virus

<400> SEQUENCE: 13
agtggtctgc ggaaccggtg a                                              21

<210> SEQ ID NO 14
<211> LENGTH: 21
<212> TYPE: DNA
<213> ORGANISM: Hepatitis C virus

<400> SEQUENCE: 14
ggtctgcgga accggtgagt a                                              21

<210> SEQ ID NO 15
<211> LENGTH: 21
<212> TYPE: DNA
<213> ORGANISM: Hepatitis C virus

<400> SEQUENCE: 15
cgaaaggcct tgtggtactg c                                              21

<210> SEQ ID NO 16
<211> LENGTH: 21
<212> TYPE: DNA
<213> ORGANISM: Hepatitis C virus

<400> SEQUENCE: 16
gaaaggcctt gtggtactgc c                                              21

<210> SEQ ID NO 17
<211> LENGTH: 21
<212> TYPE: DNA
<213> ORGANISM: Hepatitis C virus

```
<400> SEQUENCE: 17
aaaggccttg tggtactgcc t                                          21

<210> SEQ ID NO 18
<211> LENGTH: 21
<212> TYPE: DNA
<213> ORGANISM: Hepatitis C virus

<400> SEQUENCE: 18
aggccttgtg gtactgcctg a                                          21

<210> SEQ ID NO 19
<211> LENGTH: 21
<212> TYPE: DNA
<213> ORGANISM: Hepatitis C virus

<400> SEQUENCE: 19
gccttgtggt actgcctgat a                                          21

<210> SEQ ID NO 20
<211> LENGTH: 21
<212> TYPE: DNA
<213> ORGANISM: Hepatitis C virus

<400> SEQUENCE: 20
tgcgagtgcc ccgggaggtc t                                          21

<210> SEQ ID NO 21
<211> LENGTH: 21
<212> TYPE: DNA
<213> ORGANISM: Hepatitis C virus

<400> SEQUENCE: 21
gcgagtgccc cgggaggtct c                                          21

<210> SEQ ID NO 22
<211> LENGTH: 21
<212> TYPE: DNA
<213> ORGANISM: Hepatitis C virus

<400> SEQUENCE: 22
cgagtgcccc gggaggtctc g                                          21

<210> SEQ ID NO 23
<211> LENGTH: 21
<212> TYPE: DNA
<213> ORGANISM: Hepatitis C virus

<400> SEQUENCE: 23
gagtgccccg ggaggtctcg t                                          21

<210> SEQ ID NO 24
<211> LENGTH: 21
<212> TYPE: DNA
<213> ORGANISM: Hepatitis C virus

<400> SEQUENCE: 24
agtgccccgg gaggtctcgt a                                          21

<210> SEQ ID NO 25
<211> LENGTH: 21
<212> TYPE: DNA
```

```
<213> ORGANISM: Hepatitis C virus

<400> SEQUENCE: 25
gtgccccggg aggtctcgta g                                              21

<210> SEQ ID NO 26
<211> LENGTH: 21
<212> TYPE: DNA
<213> ORGANISM: Hepatitis C virus

<400> SEQUENCE: 26
tgccccggga ggtctcgtag a                                              21

<210> SEQ ID NO 27
<211> LENGTH: 21
<212> TYPE: DNA
<213> ORGANISM: Hepatitis C virus

<400> SEQUENCE: 27
gccccgggag gtctcgtaga c                                              21

<210> SEQ ID NO 28
<211> LENGTH: 21
<212> TYPE: DNA
<213> ORGANISM: Hepatitis C virus

<400> SEQUENCE: 28
ccccgggagg tctcgtagac c                                              21

<210> SEQ ID NO 29
<211> LENGTH: 21
<212> TYPE: DNA
<213> ORGANISM: Hepatitis C virus

<400> SEQUENCE: 29
cccgggaggt ctcgtagacc g                                              21

<210> SEQ ID NO 30
<211> LENGTH: 21
<212> TYPE: DNA
<213> ORGANISM: Hepatitis C virus

<400> SEQUENCE: 30
ccgggaggtc tcgtagaccg t                                              21

<210> SEQ ID NO 31
<211> LENGTH: 21
<212> TYPE: DNA
<213> ORGANISM: Hepatitis C virus

<400> SEQUENCE: 31
cgggaggtct cgtagaccgt g                                              21

<210> SEQ ID NO 32
<211> LENGTH: 21
<212> TYPE: DNA
<213> ORGANISM: Hepatitis C virus

<400> SEQUENCE: 32
gggaggtctc gtagaccgtg c                                              21

<210> SEQ ID NO 33
<211> LENGTH: 21
```

<212> TYPE: DNA
<213> ORGANISM: Hepatitis C virus

<400> SEQUENCE: 33
ggaggtctcg tagaccgtgc a                                              21

<210> SEQ ID NO 34
<211> LENGTH: 27
<212> TYPE: DNA
<213> ORGANISM: Hepatitis C virus

<400> SEQUENCE: 34
atcactcccc tgtgaggaac tactgtc                                        27

<210> SEQ ID NO 35
<211> LENGTH: 27
<212> TYPE: DNA
<213> ORGANISM: Hepatitis C virus

<400> SEQUENCE: 35
ccctgtgagg aactactgtc ttcacgc                                        27

<210> SEQ ID NO 36
<211> LENGTH: 27
<212> TYPE: DNA
<213> ORGANISM: Hepatitis C virus

<400> SEQUENCE: 36
cctgtgagga actactgtct tcacgca                                        27

<210> SEQ ID NO 37
<211> LENGTH: 27
<212> TYPE: DNA
<213> ORGANISM: Hepatitis C virus

<400> SEQUENCE: 37
gtgaggaact actgtcttca cgcagaa                                        27

<210> SEQ ID NO 38
<211> LENGTH: 27
<212> TYPE: DNA
<213> ORGANISM: Hepatitis C virus

<400> SEQUENCE: 38
ggaactactg tcttcacgca gaaagcg                                        27

<210> SEQ ID NO 39
<211> LENGTH: 27
<212> TYPE: DNA
<213> ORGANISM: Hepatitis C virus

<400> SEQUENCE: 39 cccccctcccg ggagagccat agtggtc                                       27

<210> SEQ ID NO 40
<211> LENGTH: 27
<212> TYPE: DNA
<213> ORGANISM: Hepatitis C virus

<400> SEQUENCE: 40
cgggagagcc atagtggtct gcggaac                                        27

<210> SEQ ID NO 41

```
<211> LENGTH: 27
<212> TYPE: DNA
<213> ORGANISM: Hepatitis C virus

<400> SEQUENCE: 41
gcggaaccgg tgagtacacc ggaattg                                            27

<210> SEQ ID NO 42
<211> LENGTH: 27
<212> TYPE: DNA
<213> ORGANISM: Hepatitis C virus

<400> SEQUENCE: 42
tgcgagtgcc ccgggaggtc tcgtaga                                            27

<210> SEQ ID NO 43
<211> LENGTH: 9
<212> TYPE: DNA
<213> ORGANISM: Unknown
<220> FEATURE:
<223> OTHER INFORMATION: Description of Unknown:
      Exemplary loop sequence

<400> SEQUENCE: 43 agagaactt                                                                 9

<210> SEQ ID NO 44
<211> LENGTH: 51
<212> TYPE: DNA
<213> ORGANISM: Hepatitis C virus

<400> SEQUENCE: 44
tagttcctca caggggagtg aagagaactt tcactcccct gtgaggaact a                 51

<210> SEQ ID NO 45
<211> LENGTH: 51
<212> TYPE: DNA
<213> ORGANISM: Hepatitis C virus

<400> SEQUENCE: 45
ccggttccgc agaccactat gagagaactt catagtggtc tgcggaaccg g                 51

<210> SEQ ID NO 46
<211> LENGTH: 51
<212> TYPE: DNA
<213> ORGANISM: Hepatitis C virus

<400> SEQUENCE: 46
tatggctctc ccgggagggg gagagaactt cccctcccg ggagagccat a                  51

<210> SEQ ID NO 47
<211> LENGTH: 51
<212> TYPE: DNA
<213> ORGANISM: Hepatitis C virus

<400> SEQUENCE: 47
accactatgg ctctcccggg aagagaactt tcccgggaga gccatagtgg t                 51

<210> SEQ ID NO 48
<211> LENGTH: 51
<212> TYPE: DNA
<213> ORGANISM: Hepatitis C virus

<400> SEQUENCE: 48
```
gaccactatg gctctcccgg gagagaactt cccgggagag ccatagtggt c    51

<210> SEQ ID NO 49
<211> LENGTH: 51
<212> TYPE: DNA
<213> ORGANISM: Hepatitis C virus

<400> SEQUENCE: 49
agaccactat ggctctcccg gagagaactt ccgggagagc catagtggtc t    51

<210> SEQ ID NO 50
<211> LENGTH: 51
<212> TYPE: DNA
<213> ORGANISM: Hepatitis C virus

<400> SEQUENCE: 50
ccgcagacca ctatggctct cagagaactt gagagccata gtggtctgcg g    51

<210> SEQ ID NO 51
<211> LENGTH: 51
<212> TYPE: DNA
<213> ORGANISM: Hepatitis C virus

<400> SEQUENCE: 51
ttccgcagac cactatggct cagagaactt gagccatagt ggtctgcgga a    51

<210> SEQ ID NO 52
<211> LENGTH: 51
<212> TYPE: DNA
<213> ORGANISM: Hepatitis C virus

<400> SEQUENCE: 52
tcaccggttc cgcagaccac tagagaactt agtggtctgc ggaaccggtg a    51

<210> SEQ ID NO 53
<211> LENGTH: 51
<212> TYPE: DNA
<213> ORGANISM: Hepatitis C virus

<400> SEQUENCE: 53
tactcaccgg ttccgcagac cagagaactt ggtctgcgga accggtgagt a    51

<210> SEQ ID NO 54
<211> LENGTH: 51
<212> TYPE: DNA
<213> ORGANISM: Hepatitis C virus

<400> SEQUENCE: 54
gcagtaccac aaggcctttc gagagaactt cgaaaggcct tgtggtactg c    51

<210> SEQ ID NO 55
<211> LENGTH: 51
<212> TYPE: DNA
<213> ORGANISM: Hepatitis C virus

<400> SEQUENCE: 55
ggcagtacca caaggccttt cagagaactt gaaaggcctt gtggtactgc c    51

<210> SEQ ID NO 56
<211> LENGTH: 51
<212> TYPE: DNA
<213> ORGANISM: Hepatitis C virus

<400> SEQUENCE: 56

-continued aggcagtacc acaaggcctt tagagaactt aaaggccttg tggtactgcc t    51

<210> SEQ ID NO 57
<211> LENGTH: 51
<212> TYPE: DNA
<213> ORGANISM: Hepatitis C virus

<400> SEQUENCE: 57
tcaggcagta ccacaaggcc tagagaactt aggccttgtg gtactgcctg a    51

<210> SEQ ID NO 58
<211> LENGTH: 51
<212> TYPE: DNA
<213> ORGANISM: Hepatitis C virus

<400> SEQUENCE: 58
tatcaggcag taccacaagg cagagaactt gccttgtggt actgcctgat a    51

<210> SEQ ID NO 59
<211> LENGTH: 51
<212> TYPE: DNA
<213> ORGANISM: Hepatitis C virus

<400> SEQUENCE: 59
agacctcccg gggcactcgc aagagaactt tgcgagtgcc ccgggaggtc t    51

<210> SEQ ID NO 60
<211> LENGTH: 51
<212> TYPE: DNA
<213> ORGANISM: Hepatitis C virus

<400> SEQUENCE: 60
gagacctccc ggggcactcg cagagaactt gcgagtgccc cgggaggtct c    51

<210> SEQ ID NO 61
<211> LENGTH: 51
<212> TYPE: DNA
<213> ORGANISM: Hepatitis C virus

<400> SEQUENCE: 61
cgagacctcc cggggcactc gagagaactt cgagtgcccc gggaggtctc g    51

<210> SEQ ID NO 62
<211> LENGTH: 51
<212> TYPE: DNA
<213> ORGANISM: Hepatitis C virus

<400> SEQUENCE: 62
acgagacctc ccggggcact cagagaactt gagtgccccg ggaggtctcg t    51

<210> SEQ ID NO 63
<211> LENGTH: 51
<212> TYPE: DNA
<213> ORGANISM: Hepatitis C virus

<400> SEQUENCE: 63
tacgagacct cccggggcac tagagaactt agtgccccgg gaggtctcgt a    51

<210> SEQ ID NO 64
<211> LENGTH: 51
<212> TYPE: DNA
<213> ORGANISM: Hepatitis C virus

<400> SEQUENCE: 64
ctacgagacc tcccggggca cagagaactt gtgccccggg aggtctcgta g        51

<210> SEQ ID NO 65
<211> LENGTH: 51
<212> TYPE: DNA
<213> ORGANISM: Hepatitis C virus

<400> SEQUENCE: 65
tctacgagac ctcccggggc aagagaactt tgccccggga ggtctcgtag a        51

<210> SEQ ID NO 66
<211> LENGTH: 51
<212> TYPE: DNA
<213> ORGANISM: Hepatitis C virus

<400> SEQUENCE: 66
gtctacgaga cctcccgggg cagagaactt gccccgggag gtctcgtaga c        51

<210> SEQ ID NO 67
<211> LENGTH: 51
<212> TYPE: DNA
<213> ORGANISM: Hepatitis C virus

<400> SEQUENCE: 67
ggtctacgag acctcccggg gagagaactt ccccgggagg tctcgtagac c        51

<210> SEQ ID NO 68
<211> LENGTH: 51
<212> TYPE: DNA
<213> ORGANISM: Hepatitis C virus

<400> SEQUENCE: 68
cggtctacga gacctcccgg gagagaactt cccgggaggt ctcgtagacc g        51

<210> SEQ ID NO 69
<211> LENGTH: 51
<212> TYPE: DNA
<213> ORGANISM: Hepatitis C virus

<400> SEQUENCE: 69
acggtctacg agacctcccg gagagaactt ccgggaggtc tcgtagaccg t        51

<210> SEQ ID NO 70
<211> LENGTH: 51
<212> TYPE: DNA
<213> ORGANISM: Hepatitis C virus

<400> SEQUENCE: 70
cacggtctac gagacctccc gagagaactt cgggaggtct cgtagaccgt g        51

<210> SEQ ID NO 71
<211> LENGTH: 51
<212> TYPE: DNA
<213> ORGANISM: Hepatitis C virus

<400> SEQUENCE: 71
gcacggtcta cgagacctcc cagagaactt gggaggtctc gtagaccgtg c        51

<210> SEQ ID NO 72
<211> LENGTH: 51
<212> TYPE: DNA

```
<400> SEQUENCE: 72
tgcacggtct acgagacctc cagagaactt ggaggtctcg tagaccgtgc a        51

<210> SEQ ID NO 73
<211> LENGTH: 63
<212> TYPE: DNA
<213> ORGANISM: Hepatitis C virus

<400> SEQUENCE: 73
gacagtagtt cctcacaggg gagtgataga gaacttatca ctcccctgtg aggaactact   60
gtc                                                                63

<210> SEQ ID NO 74
<211> LENGTH: 63
<212> TYPE: DNA
<213> ORGANISM: Hepatitis C virus

<400> SEQUENCE: 74
gcgtgaagac agtagttcct cacagggaga gaacttccct gtgaggaact actgtcttca   60
cgc                                                                63

<210> SEQ ID NO 75
<211> LENGTH: 63
<212> TYPE: DNA
<213> ORGANISM: Hepatitis C virus

<400> SEQUENCE: 75
tgcgtgaaga cagtagttcc tcacaggaga gaacttcctg tgaggaacta ctgtcttcac   60
gca                                                                63

<210> SEQ ID NO 76
<211> LENGTH: 63
<212> TYPE: DNA
<213> ORGANISM: Hepatitis C virus

<400> SEQUENCE: 76
ttctgcgtga agacagtagt tcctcacaga gaacttgtga ggaactactg tcttcacgca   60
gaa                                                                63

<210> SEQ ID NO 77
<211> LENGTH: 63
<212> TYPE: DNA
<213> ORGANISM: Hepatitis C virus

<400> SEQUENCE: 77
cgctttctgc gtgaagacag tagttccaga gaacttggaa ctactgtctt cacgcagaaa   60
gcg                                                                63

<210> SEQ ID NO 78
<211> LENGTH: 63
<212> TYPE: DNA
<213> ORGANISM: Hepatitis C virus

<400> SEQUENCE: 78
gaccactatg gctctcccgg gagggggaga gaacttcccc ctcccgggag agccatagtg   60
gtc                                                                63

<210> SEQ ID NO 79
```

```
<211> LENGTH: 63
<212> TYPE: DNA
<213> ORGANISM: Hepatitis C virus

<400> SEQUENCE: 79
gttccgcaga ccactatggc tctcccgaga gaacttcggg agagccatag tggtctgcgg    60
aac                                                                  63

<210> SEQ ID NO 80
<211> LENGTH: 63
<212> TYPE: DNA
<213> ORGANISM: Hepatitis C virus

<400> SEQUENCE: 80
caattccggt gtactcaccg gttccgcaga gaacttgcgg aaccggtgag tacaccggaa    60
ttg                                                                  63

<210> SEQ ID NO 81
<211> LENGTH: 63
<212> TYPE: DNA
<213> ORGANISM: Hepatitis C virus

<400> SEQUENCE: 81
tctacgagac ctcccggggc actcgcaaga gaactttgcg agtgccccgg gaggtctcgt    60
aga                                                                  63

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tctgcggaac cggtgagta                                                 19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tcaggcagta ccacaaggc                                                 19

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaaggtgaag gtcggagtc                                                 19

<210> SEQ ID NO 85
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 85
gaagatggtg atgggatttc                                                    20

<210> SEQ ID NO 86
<211> LENGTH: 31
<212> TYPE: DNA
<213> ORGANISM: Hepatitis C virus

<400> SEQUENCE: 86
ccctgtgagg aactactgtc ttcacgcaga a                                       31

<210> SEQ ID NO 87
<211> LENGTH: 29
<212> TYPE: DNA
<213> ORGANISM: Hepatitis C virus

<400> SEQUENCE: 87
tcccgggaga gccatagtgg tctgcggaa                                          29

<210> SEQ ID NO 88
<211> LENGTH: 21
<212> TYPE: DNA
<213> ORGANISM: Hepatitis C virus

<400> SEQUENCE: 88
cgaaaggcct tgtggtactg c                                                  21

<210> SEQ ID NO 89
<211> LENGTH: 34
<212> TYPE: DNA
<213> ORGANISM: Hepatitis C virus

<400> SEQUENCE: 89
tgcgagtgcc ccgggaggtc tcgtagaccg tgca                                    34
```

HEPATITIS C DSRNA EFFECTOR MOLECULES, EXPRESSION CONSTRUCTS, COMPOSITIONS, AND METHODS OF USE

CROSS REFERENCE TO RELATED APPLICATIONS PRIORITY

This application is a Continuation application of U.S. Ser. No. 12/666,057, filed on Apr. 8, 2010, now issued as U.S. Pat. No. 8,614,198, issued on Dec. 24, 2013, which is a 35 U.S.C. §371 U.S. National Phase Entry of International Application No. PCT/US2008/067871 filed on Jun. 23, 2008, which designates the U.S., and which claims the benefit under 35 U.S.C. §119(e) of U.S. Provisional Application No. 60/929,335, filed Jun. 22, 2007, the contents of which are incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 7, 2010, is named SequenceListing_TextFile_051058_048000.txt and is 28,357 bytes in size.

FIELD OF THE INVENTION

The present invention relates to nucleic acid-based therapeutics for treating or preventing Hepatitis C Virus (HCV) infection, and particularly RNAi-based therapeutics.

BACKGROUND OF THE INVENTION

Hepatitis C is an RNA virus containing a single-stranded positive-sense RNA genome of about 9,600 nts. The genes for the viral structural and non-structural proteins are flanked by 5' and 3' untranslated regions (UTRs), which are essential for genome replication. For example, the 5' UTR contains an internal ribosome entry site (IRES) which is indispensable for the initiation of HCV polyprotein translation. HCV has been classified into six major genotypes, each comprising further subgroups, which differ in their sequence homology by more than 30%. The distribution of these genotypes differs geographically. For example, genotypes 1a and 1b and the most prevalent genotypes found within the U.S., while genotypes 2 and 3 are more prevalent in other countries.

Because of the sequence variability of HCV, the development of vaccines and therapeutic drugs, including RNAi-based therapeutics, that would be active against the majority of viruses, must take advantage of the rare conserved epitopes and sequences found among the viral genotypes and quasispecies. In fact, the mutability of HCV is such that even within an infected individual, the HCV virus exists as a swarm of variants or "quasispecies" of a predominant type rather than as a single entity.

Thus, to apply a gene-silencing-based strategy to the treatment or prevention of HCV infection, it is necessary to identify sufficiently conserved stretches of nucleotide sequence in this highly mutable virus. That is, since RNA interference is a sequence-specific effect, therapeutic or prophylactic RNAi molecules must be specific for HCV target sequences, despite the fact that hepatitis C viral genomes are highly variable. While HCV target sequence conservation is an important consideration in the design of sequence-specific anti-HCV prophylactic or therapeutic modalities such as RNAi or antisense, e.g., some of the highly conserved regions of the HCV genome such as the 5' UTR are known to be highly structured, while some regions of the viral genome are present in the infected cell in association with proteins which make them largely inaccessible to antisense or RNAi. The lack of a readily available HCV animal model and problems with various HCV cell culture models, e.g., the absence or deficiencies in viral infection or replication models, have hindered the development of anti-HCV pharmaceuticals of all types.

Despite well over a decade of research efforts, there are no vaccines available for HCV. As a consequence, the rate of new HCV infections around the world is extremely high. The WHO estimates that globally 170 million individuals carry chronic HCV infections and that new infections are established at a rate of 3 to 4 million annually.

Chronic HCV infection induces liver inflammation, causing progressive liver disease that can lead to cirrhosis and hepatocellular carcinoma (liver cancer). Chronic HCV infection becomes established in 75%-85% of individuals experiencing an initial infection, and HCV-related liver failure is the most common indication cited for liver transplantation in the U.S. Chronic HCV infection in its early stages may cause only mild non-specific symptoms, such as fatigue, or be completely asymptomatic, leaving many infected individuals unaware that they carry a dangerous chronic infection.

Current therapies for HCV infection, which may include a 6 to 12 month regimen of pegylated interferon and ribavirin, can lead to a cure in a minority of patients. Response rates vary by HCV genotype, with genotype 2 and 3 patients exhibiting a 76% response rate to the current standard therapy while patients infected with genotype 1a and 1b having only a 46% response rate. Unfortunately, genotype 1 accounts for 60% of global infections and is the dominant strain in the U.S., Japan, and Western Europe. Complicating genotype 1 resistance to ribavarin and interferon is the fact that both drugs have side effect profiles that can require dose reduction or discontinuance of therapy when patients experience side effects. Further complicating patient outcomes is the fact that patients who fail an initial treatment regimen rarely respond favorably to a subsequent round of treatment with interferon and ribavarin.

Clinicians who treat HCV patients are hopeful that current and future research programs will yield options that improve the response rate for genotype 1 patients, which is currently less than 50% using ribavarin and interferon. New treatment options that have a more tolerable side effect profile would improve patient compliance and enable more patients to complete a full course of therapeutic intervention.

There remains a need for treatment options for HCV-exposed or infected patients, including for highly conserved nucleic acid-based molecules, including double-stranded RNAs and constructs encoding dsRNAs, capable of inhibiting the replication of HCV in mammalian cells. Such nucleic acid based anti-HCV therapeutic agents have the potential to improve patient response rates to therapy, improve adverse event profile, and eliminate or significantly delay the development of drug resistant escape mutant virus.

SUMMARY OF THE INVENTION

The present invention provides agents, compositions, constructs, and methods for silencing HCV polynucleotides, as well as methods and compositions capable of inhibiting HCV replication and for treating or preventing HCV infection in a mammalian cell.

In one aspect, the present invention provides an agent or composition for silencing HCV RNA in a cell. In one aspect, the agent or composition inhibits HCV viral replication and antigen expression in a mammalian cell, preferably a human cell. In this aspect, the agent or composition comprises at least one double-stranded RNA effector molecule or complex. The double-stranded RNA effector molecule or complex comprises: (1) a sequence of at least 19, 20, or 21 consecutive nucleotides having at least 90%, 95%, or 100% identity with a nucleotide sequence within HCV Conserved Region 1 (SEQ ID NO: 2), HCV Conserved Region 2 (SEQ ID NO: 3), HCV Conserved Region 5 (SEQ ID NO: 4), active target region (ATR)-1 (SEQ 10 NO: 86), ATR-2 (SEQ 10 NO: 87), ATR-3 (SEQ 10 NO: 88), or ATR-4 (SEQ 10 NO: 89); and (2) its complementary sequence. Preferably the dsRNA effector molecule will include (1) a sequence of 19 to 29, 19 to 25, 20 to 25, 21 to 25, or 21 to 23 consecutive nucleotides within HCV Conserved Region 1 (SEQ 10 NO: 2), HCV Conserved Region 2 (SEQ 10 NO: 3), HCV Conserved Region 5 (SEQ 10 NO: 4), active target region (ATR)-1 (SEQ 10 NO: 86), ATR-2 (SEQ 10 NO: 87), ATR-3 (SEQ 10 NO: 88), or ATR-4 (SEQ 10 NO: 89); and (2) its complementary sequence. The effector molecule may optionally form a stem-loop structure, with the sequence of at least 19 nucleotides and its complementary sequence being connected via a loop sequence, thereby providing, for example, short-hairpin RNAs (shRNAs) suitable for RNAi-based HCV therapeutics. In one aspect, multiple different of such dsRNA effector molecules of the invention, e.g., two, three, four, five or more, are administered to or expressed concomitantly in a mammalian cell, to eliminate or substantially delay the emergence of drug resistant viral escape mutants.

In another aspect, the present invention provides a construct suitable for replication in a host cell, and/or suitable for expression of an RNA molecule of the invention in vitro or in vivo. The construct of the invention encodes at least one RNA effector molecule of the invention, which may be operably linked to a promoter sequence, such as an RNA Polymerase I, RNA polymerase II, or RNA polymerase Ill promoter sequence as described herein. In one aspect, multiple such dsRNA effector molecules of the invention, e.g., hairpin dsRNA molecules, are encoded by a single expression construct under the control of one or more of such promoters.

In a third aspect, the present invention provides a method for silencing or inhibiting the replication of HCV, including inhibition of HCV RNA and/or HCV antigen expression, in a mammalian cell. In this aspect, the method of the invention comprises administering to the mammalian cell an agent, composition, or construct of the invention in a manner and amount effective to inhibit HCV replication and/or HCV RNA or antigen expression in the cell. In a related aspect, the present invention provides a method for treating or preventing HCV infection in a patient, comprising administering to the patient an effective amount and regimen of an agent, composition, or construct of the invention as described herein.

The present invention further provides methods for preparing the dsRNA effector molecules, compositions, and constructs of the invention.

DETAILED DESCRIPTION OF THE INVENTION

Figure 1:
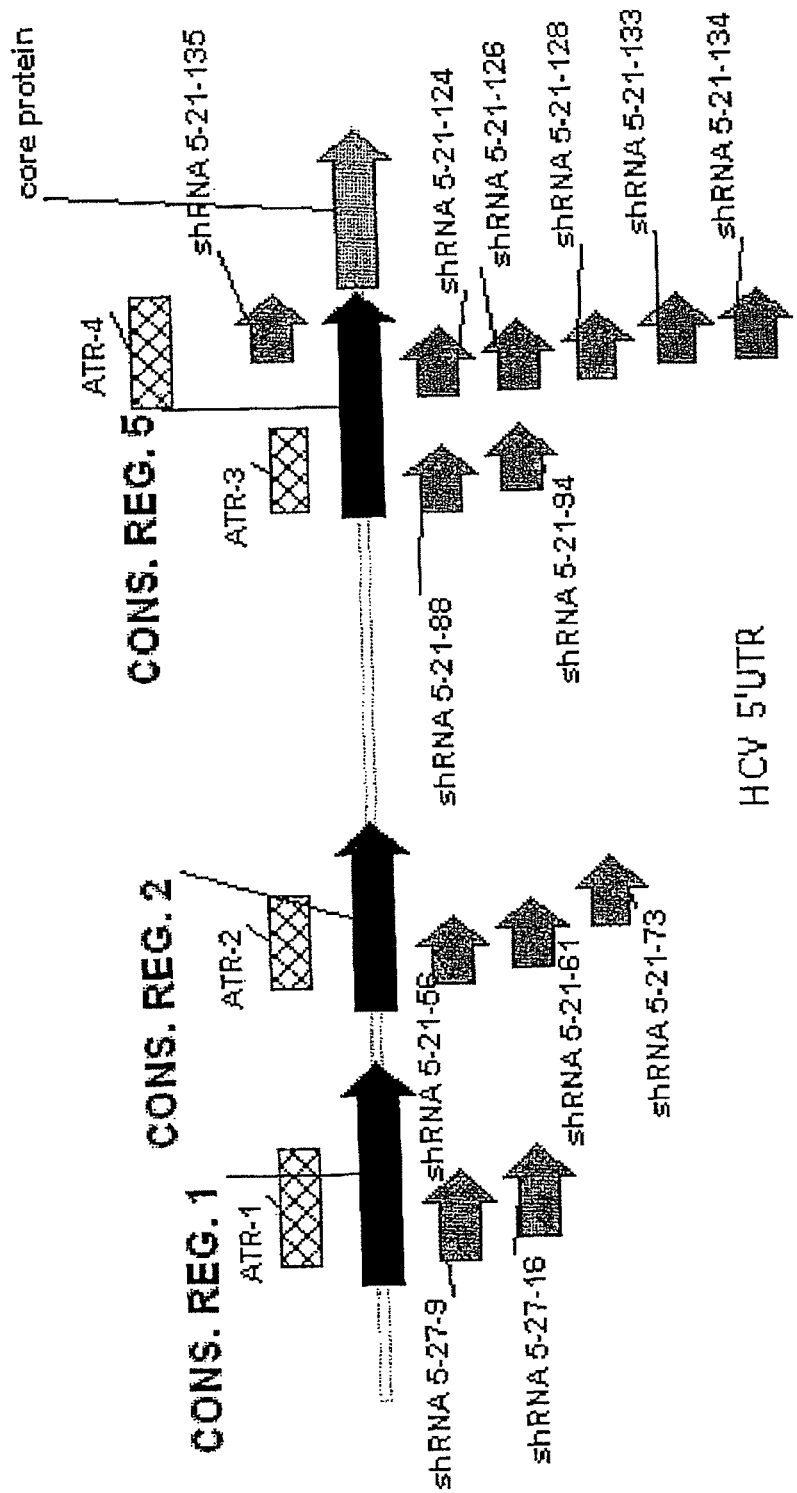
FIG. 1 shows a number of highly active shRNAs which map to four active target regions (ATR-1, ATR-2, ATR-3, and ATR-4) within the HCV 5' UTR.

To identify sequences that are most conserved among HCV genomes worldwide, a bioinformatic analysis was conducted. There are 93 complete genomes published in GenBank version 134.0 and these were compared for the identification of sequences of 19 nts or greater that are >95% conserved, and which could potentially serve as target sites for small inhibitory RNAs (siRNAs) and short-hairpin RNAs (shRNAs). The following sequences were identified within the HCV 5'UTR, and are shown with respect to GenBank Accession ID AB047639 (SEQ ID NO: 1).

```
HCV Conserved region 1: nts 35-102 of AB047639.
                                        (SEQ ID NO: 2)
5'-atcactccccctgtgaggaactactgtcttcacgcagaaagcgcct
agccatggcgttagtatgagtgt-3'

HCV Conserved region 2: nts 119-176 of AB047639.
                                        (SEQ ID NO: 3)
5'-ccccccctcccgggagagccatagtggtctgcggaaccggtgagta
caccggaattgc-3'

HCV Conserved region 5: nts 270-338 of AB047639.
                                        (SEQ ID NO: 4)
5'-gcgaaaggccttgtggtactgcctgatagggcgcttgcgagtgcc
ccgggaggtctcgtagaccgtgca-3'
```

Four highly conserved and highly active target regions (ATR), preferred for some applications, were identified:
ATR-1: 5'-CCCTGTGAGGAACTACTGTCTTCACGCA-GAA-3' (SEQ ID NO: 86), mapping to nucleotide coordinates 42 to 76 of GenBank Accession No. AB047639, found within Conserved Region 1 (SEQ ID NO: 2).
ATR-2: 5'-TCCCGGGAGAGCCATAGTGGTCTGCG-GAA-3' (SEQ ID NO: 87), mapping to nucleotide coordinates 126 to 154 of GenBank Accession No. AB047639, found within Conserved Region 2 (SEQ ID NO: 3).
ATR-3: 5'-CGAAAGGCCTTGTGGTACTGC-3', (SEQ ID NO: 88) mapping to nucleotide coordinates 271 to 297 of GenBank Accession No. AB047639, found within Conserved Region 5 (SEQ ID NO: 4).
ATR-4: 5'-TGCGAGTGCCCCGGGAGGTCTCGTAGAC-CGTGCA-3', (SEQ ID NO: 89) mapping to nucleotide coordinates 305 to 338 of GenBank Accession No. AB047639, found within Conserved Region 5 (SEQ ID NO: 4).

In this context, the present invention provides agents, compositions, constructs and methods for silencing HCV polynucleotides, as well as for treating or preventing HCV infection in a mammalian cell.

Effector RNA Molecules and Complexes

In one aspect, the present invention provides an agent for silencing HCV RNA in a cell. The agent comprises at least one double-stranded RNA effector molecule or complex, which comprises: (1) a sequence of at least 19, 20, or 21 consecutive nucleotides having at least about 90% identity with a nucleotide sequence within HCV Conserved Region 1 (SEQ ID NO: 2), HCV Conserved Region 2 (SEQ ID NO: 3), HCV Conserved Region 5 (SEQ ID NO: 4), ATR-1 (SEQ ID NO: 86), ATR-2 (SEQ ID NO: 87), ATR-3 (SEQ ID NO: 88), or ATR-4 (SEQ ID NO: 89) and (2) its complementary sequence.

In this context, the nucleotide "t" in SEQ ID NOS: 1, 2, 3, 4, etc. is considered to be identical with "u," which would take the place of "t" in the corresponding RNA sequence. Thus, throughout this application it will be understood that where RNA sequences are described for convenience with respect to encoding or corresponding DNA sequences, "t" will be replaced by "u" in the RNA sequence.

In certain embodiments, the at least 19 nucleotides of the dsRNA effector molecule or complex has at least about 95% identity with a nucleotide sequence within HCV Conserved Region 1 (SEQ ID NO: 2), HCV Conserved Region 2 (SEQ ID NO: 3), HCV Conserved Region 5 (SEQ ID NO: 4), ATR-1 (SEQ ID NO: 86), ATR-2 (SEQ ID NO: 87), ATR-3 (SEQ ID NO: 88), or ATR-4 (SEQ ID NO: 89), such as at least about 96%, 97%, 98%, 99%, or about 100% identity. Identity between two nucleotide sequences may be determined using any suitable algorithm known in the art, such as Tatusova et al., Blast 2 sequences—a new tool for comparing protein and nucleotide sequences, *FEMS Microbial Lett.* 174:247-250 (1999).

In some embodiments, the at least 19 nucleotides of the dsRNA effector molecule or complex has a sequence selected from within nucleotides 42-76 (ATR-1), 126-154 (ATR-2), 271 to 297 (ATR-3), 305 to 338 (ATR-4) or 271-338 of SEQ ID NO: 1 (GenBank Accession ID AB047639). For example, the dsRNA effector molecule or complex may comprise at least 19 nucleotides selected from within nucleotides 305-338 of SEQ ID NO: 1.

The dsRNA effector molecules and complexes may have double-stranded regions that vary somewhat in length, so long as the effector molecule or complex is effective for silencing the target polynucleotide, that is, the length of the double-stranded region is generally sufficient to trigger RNAi-mediated degradation of the target sequence. For example, the agent or composition of the invention may comprise at least one double-stranded RNA effector molecule or complex containing a double-stranded region of from 19 or 21 base pairs to about 30 or 40 base pairs, or from 21 base pairs to about 27 base pairs. In certain embodiments, the double-stranded RNA effector molecule or complex contains a double-stranded region of about 21 or about 27 base pairs.

In accordance with the invention, the double-stranded RNA molecules and complexes of the invention may exist in a denatured or substantially denatured form.

Alternatively, the double-stranded RNA molecules and complexes may exist in a double-stranded conformation, or a substantially double-stranded conformation, or a partially double-stranded conformation, at least with respect to the regions of complementarity. Generally, the RNA molecules and complexes of the invention are capable of forming double-stranded structures under physiological conditions (e.g., intracellular conditions), where these structures are sufficient to trigger RNAi-mediated gene silencing.

In some embodiments, the double-stranded RNA effector molecule or complex has a double-stranded region that comprises, or consists essentially of (or consists of) in one strand, a sequence selected from SEQ ID NOS: 5-42 as disclosed herein. Such sequences, which correspond to HCV Conserved Regions 1, 2, and 5, are listed in Table 3.

The double-stranded RNA effector molecules of the invention comprise a region of self-complementarity such that nucleotides in one segment of the molecule base pair with nucleotides in another segment of the molecule (e.g., stem-loop or hairpin structure as described herein). In contrast, the double-stranded RNA effector duplexes or complexes of the invention include at least two separate polynucleotide strands that have a region of complementarity to each other. The double-stranded RNA complexes (i.e., duplexes) may be fully complementary, that is, may contain no single stranded regions, such as single stranded ends. In other embodiments, the double-stranded RNA complex contains short single-stranded ends, such as single-stranded 5' or 3' ends of from about 1 to about 5 nucleotides (e.g., 1, 2, or 3 nucleotides).

In certain embodiments, the effector molecule is a short hairpin dsRNA (shRNA) or a microRNA. A "shRNA" (short-hairpin RNA) is an RNA molecule of less than approximately 200 or 100 nucleotides, such as about 70 nucleotides or less, in which at least one stretch of nucleotides (e.g., at least about 19 nucleotides) is base paired with a complementary sequence located on the same RNA molecule and separated from the complementary sequence by an unpaired region. These single-stranded hairpin regions form a single-stranded loop between the stem structure created by the two regions of base complementarity.

The length and nucleotide sequence of the loop sequence is not narrowly critical, and may range, for example, from about 4 to 5 to about 20 nucleotides in length, or from about 7 to about 10 nucleotides in length. For example, the loop sequence may be about 9 nucleotides in length. An exemplary loop sequence is 5'-agagaactt-3' (SEQ ID NO: 43). The loop may vary considerably in length and sequence, although loop sequences which assume significant secondary structure are to be avoided, as are poly T (e.g., $T_4$ to $T_5$ or more) sequences, which might trigger premature termination of transcription for effector molecules expressed by polymerase III promoters. In addition to a "stem" region which comprises the identified homologous and complementary HCV sequences, in certain embodiments the hairpin molecule and/or the expression vector encoding the hairpin RNA will include additional 5' and/or 3' sequences, including in some embodiments 5' and/or 3' flanking sequences as well as loop sequences derived from miRNAs. See e.g., US 2004/0053411, the teaching of which is hereby incorporated by reference.

Exemplary shRNAs in accordance with the invention have a sequence selected from SEQ ID NOS: 44-81. The complementary strand may also, optionally, have from one to five uracil nucleotides at its 3'-end, which may correspond to transcribed transcription termination sequences.

In addition to single shRNAs, the invention includes dual or bi-finger and multi-finger hairpin dsRNAs, in which the RNA molecule comprises two or more of such stem-loop structures, each separated by a single-stranded spacer region. In some embodiments such two or more stem-loop structures may be encoded by an expression construct and operably linked to a single promoter. Thus, the hairpin dsRNA may be a single hairpin dsRNA or a bi-fingered, or multi-fingered dsRNA hairpin as described in PCT/US03/033466 or WO 04/035766, or a partial or forced hairpin structure as described in WO 2004/011624, the disclosures of which are hereby incorporated by reference. In these embodiments, the multi-finger hairpin RNA contains two, three, or four double stranded regions, each corresponding to an HCV target sequence independently selected from SEQ ID NOS: 5-42, such as SEQ ID NOS: 11, 19, 22, and 33. In these multi-finger hairpin RNAs the stem loop sequences may be independently selected from SEQ ID NOS: 44-81.

HCV target sequences (as described above) may also be combined into other RNA structures suitable for RNAi-based therapeutics, including a single stem loop structure with multiple double-stranded regions separated by mismatch region(s). Such RNA structures are disclosed in U.S. application Ser. No. 10/531,349, which was published as US 2006/0035344 on Feb. 16, 2006, which is hereby incorporated by reference. In these embodiments, the multi-target effector molecule may comprise two, three, or four double-stranded regions each corresponding to an HCV target sequence (as described herein) independently selected from SEQ 10 NOS: 5-42, such as SEQ 10 NO: 11, 19, 22, and 33.

The RNA molecules and complexes of the invention may be composed purely or predominately of ribonucleotides found naturally in RNA (A, U, C, G), or may contain chemically modified nucleotides. Exemplary chemically modified nucleotides include phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These, as well as other chemical modifications, support RNAi-mediated gene silencing while having superior serum stability.

RNA Compositions

The invention further provides compositions containing from two to five double-stranded RNA effector molecules or complexes, such as from two to five double-stranded RNA effector molecules or complexes as described above. For example, the two to five double-stranded RNA effector molecules (e.g., shRNAs) or complexes may each comprise: (1) a sequence of at least 19 nucleotides having at least 90% identity with a nucleotide sequence within Conserved Region 1 (SEQ 10 NO: 2), Conserved Region 2 (SEQ 10 NO: 3), Conserved Region 5 (SEQ 10 NO: 4); ATR-1 (SEQ 10 NO: 86), ATR-2 (SEQ 10 NO: 87), ATR-3 (SEQ 10 NO: 88), or ATR-4 (SEQ 10 NO: 89), and (2) its complementary sequence. Where the two to five double-stranded RNAs are each shRNAs, the shRNAs each further comprise a loop sequence as described above.

Thus, the composition of the invention may contain a plurality of double-stranded RNA effector molecules, each having a double-stranded region that comprises (or consists essentially of) a sequence independently selected from SEQ 10 NOS: 5-42, and its complementary sequence. An exemplary composition may have: a first dsRNA effector molecule comprising SEQ 10 NO: 11 and its complementary sequence; a second dsRNA effector molecule comprising SEQ 10 NO: 19 and its complementary sequence; a third dsRNA effector molecule comprising SEQ 10 NO: 22 and its complementary sequence; and a fourth dsRNA effector molecule comprising SEQ 10 NO: 33 and its complementary sequence. One, two, three, or four of these double stranded RNA effector molecules may be in the form of short-hairpin RNAs, that is, the sense and anti-sense strands may be connected by a short loop sequence as described herein. Thus, in these embodiments, the composition of the invention may comprise from two to five (e.g., four) double-stranded RNA effector molecules independently selected from SEQ ID NOS: 44-81. For example, the composition may comprise the four shRNAs represented by the sequences: SEQ ID NO: 50, SEQ ID NO: 58, SEQ ID NO: 61, and SEQ ID NO: 72. In some embodiments the plurality of anti-HCV RNA effector molecules are expressed from a plasmid or viral vector within a human cell.

Alternatively still, the composition of the invention may contain a plurality of double-stranded RNA effector duplexes or complexes, each having a double-stranded region that comprises (or consists essentially of) a sequence independently selected from SEQ ID NOS: 5-42, and its complementary sequence. For example: a first RNA effector complex may comprise, in one RNA strand, the nucleotide sequence of SEQ ID NO: 11; a second RNA effector complex may comprise, in one strand, the nucleotide sequence of SEQ ID NO: 19; a third RNA effector complex may comprise, in one strand, the nucleotide sequence of SEQ ID NO: 22; and a fourth RNA effector complex may comprise, in one strand, the nucleotide sequence of SEQ ID NO: 33. Such RNA molecules are base-paired in the complex with (or are capable of base-pairing with) a complementary or partially complementary RNA molecule in the complex, that is an RNA molecule having a sequence complementary to SEQ ID NOS: 11, 19, 22, and 33, respectively.

Constructs

In another aspect, the present invention provides a construct encoding at least one RNA molecule or complex of the invention. The construct may be, for example, a plasmid or viral vector. Such constructs may be expression constructs suitable for expression of the encoded RNA in vitro or in vivo, or may otherwise be suitable for replication of the construct in a host cell, such as a prokaryotic or eukaryotic host cell, including bacteria, yeast, and mammalian including human host cells. The construct may include an origin of replication, mechanism for selection (e.g., antibiotic resistance gene) as well as elements to facilitate removal of the RNA-encoding sequence for sub-cloning into additional constructs or vectors as may be desired, such as conveniently placed restriction endonuclease cleavage sites (e.g., flanking the RNA-encoding sequence(s)).

In some embodiments, the construct is an expression construct containing a DNA segment that encodes an RNA molecule of the invention, with the DNA segment being operably linked to a promoter to drive expression of the RNA molecule. An "expression construct" is any double-stranded DNA or double-stranded RNA designed to produce an RNA of interest. The invention includes expression constructs in which one or more of the promoters is not in fact operably linked to a polynucleotide sequence to be transcribed, but instead is designed for efficient insertion of an operably-linked polynucleotide sequence to be transcribed by the promoter, for instance by way of one or more restriction cloning sites in operative association with the one or more promoters.

Transfection or transformation of the expression construct into a recipient cell allows the cell to express an RNA effector molecule encoded by the expression construct. An expression construct may be a genetically engineered plasmid, virus, recombinant virus, or an artificial chromosome derived from, for example, a bacteriophage, adenovirus, adena-associated virus, retrovirus, lentivirus, poxvirus, or herpesvirus. Expression vectors for use with the invention contain sequences from bacteria, viruses or phages. Such vectors include chromosomal, episomal and virus-derived vectors, e.g., vectors derived from bacterial plasmids, bacteriophages, yeast episomes, yeast chromosomal elements, and viruses; as well as vectors derived from combinations thereof, such as those derived from plasmid and bacteriophage genetic elements, cosmids and phagemids. Exemplary vectors are double-stranded DNA phage vectors and double-stranded DNA viral vectors.

In certain embodiments, the expression construct of the invention is a plasmid, such as a plasmid suitable for delivery to and/or for RNA expression in a mammalian cell.

The construct of the invention encodes at least one double-stranded RNA effector molecule, which comprises: (1) a sequence of at least 19 nucleotides having at least about 90% identity with a nucleotide sequence within HCV Conserved Region 1 (SEQ ID NO: 2), HCV Conserved Region 2 (SEQ ID NO: 3), HCV Conserved Region 5 (SEQ 10 NO: 4); ATR-1 (SEQ 10 NO: 86), ATR-2 (SEQ 10 NO: 87), ATR-3 (SEQ 10 NO: 88), or ATR-4 (SEQ 10 NO: 89), and (2) its complementary sequence.

In certain embodiments, the at least 19 nucleotides have at least about 95% identity with a nucleotide sequence within HCV Conserved Region 1 (SEQ10 NO: 2), HCV Conserved Region 2 (SEQ 10 NO: 3), HCV Conserved Region 5 (SEQ 10 NO: 4), ATR-1 (SEQ 10 NO: 86), ATR-2 (SEQ 10 NO: 87), ATR-3 (SEQ10 NO: 88), or ATR-4 (SEQ 10 NO: 89), such as at least about 96%, 97%, 98%, 99%, or about 100% identity. Identity between two nucleotide sequences may be determined using any suitable algorithm known in the art, such as Tatusova et al., *Blast 2 sequences—a new tool for comparing protein and nucleotide sequences, FEMS Microbial Lett.* 174: 247-250 (1999).

In some embodiments, the at least one RNA effector molecule encoded by the construct or vector has a sequence selected from within nucleotides 42-76, 126-154, or 271-338 of SEQ 10 NO: 1 (GenBank Accession 10 AB047639). For example, the construct may encode an RNA effector molecule comprising at least 19 nucleotides selected from within nucleotides 305-338 of SEQ 10 NO: 1.

The expression construct of the invention may encode RNA effector molecules having double-stranded regions that vary somewhat in length, so long as the effector molecule is effective for silencing the target polynucleotide. For example, the expression construct may encode at least one double-stranded RNA effector molecule containing a double-stranded region of from 19 or 21 base pairs to about 30 or 40 base pairs, or from 21 to about 27 base pairs. In certain embodiments, the double-stranded RNA effector molecule contains a double-stranded region of about 21 or about 27 base pairs.

In some embodiments, the construct (e.g., expression vector) encodesone or more double-stranded RNA effector molecules, each having a double-stranded region that comprises, or consists essentially of (or consists of) in one strand, a sequence selected from SEQ 10 NOS: 5-42. Such sequences are listed in Table 3. In some embodiments, the expression vector encodes at least one double stranded RNA effector molecule that comprises: 1) a sequence selected from SEQ 10 NO: 9, 11, 19, 22, 26, 31, 32, and 33; 2) the complement of said sequence, and optionally, 3) a sequence linking 1) and 2). In some embodiments, the expression vector will encode at least two, three, four, or more of such dsRNA effector molecules. In some embodiments the expression vector will encode at least four different dsRNA effector molecules comprising, in double stranded conformation, SEQ 10 NOS: 11, 19, 22, and 33; SEQ 10 NOS: 9, 11, 31, and 33; SEQ 10 NOS: 11, 19, 31, and 33; SEQ 10 NOS: 19, 22, 32, and 33; SEQ 10 NOS: 11, 19, 22, and 33; or SEQ 10 NOS: 26, 31, 32, and 33.

The encoded double stranded RNA effector molecule(s) may be composed of two separate complementary, or partially complementary RNA molecules (e.g., expressed from separate expression cassettes on the same or different vectors), or may alternatively be in the form of a single RNA molecule, such as a short-hairpin RNA. In the latter embodiment, the sense and anti-sense polynucleotides are connected via a loop sequence, which is generally single-stranded.

The length of the loop sequence is not narrowly critical, and may range, for example, from 4 to 20 nucleotides in length, or from 7 to 10 nucleotides in length, or longer if desired, e.g., 30 nt, 40 nt, etc. For example, the loop sequence may be about 9 nucleotides in length. An exemplary loop sequence is 5'-agagaactt-3' (SEQ 10 NO: 43). The loop sequence may also vary considerably, so long as structure-forming complementarity is avoided, and, in the case of RNA polymerase Ill promoter transcribed sequences, poly T termination sequences are avoided.

In accordance with this aspect of the invention, exemplary expression constructs encode double-stranded RNA effector molecule(s) having a sequence selected from SEQ 10 NOS: 44-81. The complementary strand may also, optionally have from 1 to 5 uracil nucleotides at its 3'-end, representing transcribed RNA pol Ill termination signal nucleotides. The expressed dsRNA effector molecule may also optionally include one to five or more additional 5' nucleotides, which may vary depending on the transcription start site.

The expression construct may be engineered to encode multiple, e.g., three, four, five or more RNA molecules, such as the RNA molecules described herein, including short hairpin dsRNAs. The expression construct may include a plurality of promoters, e.g., RNA polymerase I, II or Ill promoters, mitochondrial promoters, etc., operable in the host mammalian cell. Each promoter may be operably linked to a sequence encoding one or more RNA molecules of the invention, followed by an appropriate termination sequence. In addition to targeting highly conserved HCV sequences, the ability to co-deliver two, three, four, five or more different RNA effector molecules radically reduces the ability of the virus to develop escape mutants. While "cocktail" pharmaceutical preparations including multiple active components can be formulated, dsRNA expression constructs provide an attractive delivery vehicle for accomplishing such co-delivery of a plurality of different antiviral effector molecules by a single pharmaceutical entity. The manufacturing and regulatory advantages of such an approach are readily apparent.

In certain embodiments, the expression construct encodes two or more RNAs of the invention, such as 2, 3, 4, 5, or more double stranded RNA molecules, such as shRNAs. Thus, the expression construct may encode double stranded RNAs, such as shRNA hairpins, specific for one or more of HCV Conserved Regions 1, 2 or 5, or ATR-1, ATR-2, ATR-3, or ATR-4.

In these embodiments, the invention provides one or more expression constructs, which collectively encode from two to five or more double-stranded RNA effector molecules, such as from two to five or more double-stranded RNA effector molecules as described herein. In certain embodiments, each expression construct encodes two, three, or four double-stranded RNA effector molecules, and preferably shRNAs. The encoding sequences, which may each be operably linked to a promoter, may each encode: (1) a sequence of at least 19 nucleotides having at least 90% identity with a nucleotide sequence within HCV Conserved Region 1 (SEQ 10 NO: 2), HCV Conserved Region 2 (SEQ 10 NO: 3), or HCV Conserved Region 5 (SEQ 10 NO: 4), ATR-1 (SEQ 10 NO: 86), ATR-2 (SEQ 10 NO: 87), ATR-3 (SEQ 10 NO: 88), or ATR-4 (SEQ 10 NO: 89); (2) its complementary sequence; and optionally (3) a loop sequence.

For example, the expression construct of the invention may encode a plurality of double-stranded RNA effector molecules having double-stranded regions comprising (or consisting essentially of) a sequence independently selected from SEQ 10 NOS: 5-42 and its complementary sequence. In one embodiment, the construct encodes: a first effector molecule comprising or consisting essentially of (or consisting of) the nucleotide sequence of SEQ 10 NO: 11, a second effector molecule comprising or consisting essentially of (or consisting of) the nucleotide sequence of SEQ IO NO: 19, a third effector molecule comprising or consisting essentially of (or consisting of) the nucleotide sequence of SEQ ID NO: 22, and a fourth effector molecule comprising or consisting essentially of (or consisting of) the nucleotide sequence of SEQ ID NO: 33. One, two, three, or four of these double stranded RNA effector molecules may be in the form of short-hairpin RNAs, that is, having sense and anti-sense strands connected by a short loop sequence as described herein. Thus, in these embodiments, the expression construct of the invention may encode a plurality of dsRNA effector molecules independently selected from SEQ ID NOS: 44-81. The construct may encode two, three, or four double-stranded RNA effector molecules represented by the sequences: SEQ ID NO: 50, SEQ ID NO: 58, SEQ ID NO: 61, and SEQ ID NO: 72.

The expression construct may encode an RNA molecule of the invention and its complementary stand separately, that is from separate promoters (e.g., separate expression cassettes). In this embodiment, the double-stranded molecule is produced intracellularly upon expression of the RNAs and subsequent hybridization. Typically, with expressed interfering RNA (eiRNA), the dsRNA is expressed in the first transfected cell from an expression vector. In such a vector, the sense strand and the antisense strand of the dsRNA may be transcribed from the same nucleic acid sequence using e.g., two convergent promoters at either end of the nucleic acid sequence or separate promoters transcribing either a sense or antisense sequence. Alternatively, two plasmids can be cotransfected, with one of the plasmids designed to transcribe one strand of the dsRNA while the other is designed to transcribe the other strand.

In certain embodiments, the construct is an expression construct suitable for expression (e.g., transcription) of the encoded RNA in vitro or in vivo. In these embodiments, the construct encodes an RNA molecule of the invention operably linked to a promoter sequence. Suitable promoter sequences suitable for run-off transcription in vitro are known, and include T3 and T7 promoters. In other embodiments, the expression construct encodes an RNA molecule of the invention operably linked to a promoter suitable for expression (e.g., transcription) of the RNA in a mammalian cell. The mammalian cell may be in culture, or may be a patient's cell, e.g., a patient afflicted with or at risk of acquiring HCV. Promoters suitable for RNA expression in a mammalian cell are known, and include those described in WO 2006/033756, which is hereby incorporated by reference. For example, the construct of the invention may contain a DNA sequence encoding an RNA molecule of the invention operably linked to an RNA polymerase Ill promoter, a 7SK promoter, an H1 promoter, or a U6 promoter. Further, where the construct encodes a plurality of RNA molecules, each independently controlled by its own promoter, the promoters may be the same or different. In one aspect, an expression construct may comprise two, three, four or more 7SK 4A promoters as described in WO 2006/033756. Additional promoters may be selected from an RNA polymerase I promoter, an RNA polymerase II promoter, a T7 polymerase promoter, an SP6 polymerase promoter, a tRNA promoter, and a mitochondrial promoter.

Generally, vector-directed expression of short RNA effector molecules including short hairpin dsRNAs is most efficient when under the control of a mammalian promoter that the host cell naturally employs for expression of small RNA molecules. These promoters comprise the family of RNA Polymerase III promoters, including Type 1, Type 2, and Type 3 RNA Polymerase Ill promoters.

Prototypical examples of promoters in each class are found in genes encoding 5s RNA (Type 1), various transfer RNAs (Type 2) and U6 small nuclear RNA (Type 3). Another promoter family (transcribed by RNA Polymerase I) is also dedicated in the cell to transcription of small structural RNAs; however, this family may be less diverse in sequence than the RNA Polymerase Ill promoters. Finally, RNA Polymerase II promoters are used in the transcription of the protein-coding messenger RNA molecules, as distinguished from the small structural and regulatory RNA mentioned above. The majority of promoter systems known in the art utilize RNA Polymerase II promoters, which may not be preferred for production of small RNAs. An exception may be shRNAs expressed by RNA polymerase II or Ill promoters in a miRNA context as taught in e.g. U.S. Ser. No. 10/429,249 and PCT/US2007/81103, which is hereby incorporated by reference. RNA polymerase Ill promoter-based vectors containing one promoter have been described in the art (see, e.g., U.S. Pat. No. 5,624,803, Noonberg et al., "In vivo oligonucleotide generator, and methods of testing the binding affinity of triplex forming oligonucleotides derived therefrom"), and a description of US-based vector systems can be found in Lee et al., Nat. Biotechnol. 20:500-05 (2002). Yu et al., Proc. Natl. Acad. Sci. USA 99:6047-52 (2002), describe an expression system for short duplex siRNAs comprising a T7 and U6 promoter. Miyagishi and Taira, Nat. Biotechnol. 20:497-500 (2002), describe expression plasmids for short duplex siRNAs comprising expression cassettes containing tandem U6 promoters, each transcribing either the sense or the antisense strand of an siRNA, which are then annealed to form duplex siRNAs. Where it is desired to deliver short dsRNAs, multiple RNA polymerase III promoter expression constructs (as taught in WO 06/033756, which is hereby incorporated by reference), may be used in accordance with the invention. The multiple RNA polymerase Ill promoters may be utilized in conjunction with promoters of other classes, including RNA polymerase I promoters, RNA polymerase II promoters, etc. Preferred in some applications are the Type III RNA pol Ill promoters including U6, H1, and 7SK, which exist in the 5' flanking region, include TATA boxes, and lack internal promoter sequences. A preferred 7SK promoter is the 7SK 4A promoter variant taught in WO 06/033756, the nucleotide sequence of which is hereby incorporated by reference. In such expression constructs each promoter may be designed to control expression of an independent RNA expression cassette, e.g., a shRNA expression cassette.

Such multiple RNA polymerase Ill promoter expression constructs are suitable for expression of multiple, e.g., three, four, five, or more anti-HCV shRNA effector molecules of the invention. Each dsRNA effector molecule, e.g., hairpin dsRNA, may be transcribed from its own promoter or one or more promoters may be engineered to each transcribe a single RNA strand encoding a series or "gang" of two, three or more shRNA molecules separated by single-stranded regions. RNA Pol Ill promoters may be especially beneficial for expression of small engineered RNA transcripts, because RNA Pol Ill termination occurs efficiently and precisely at a short run of thymine residues in the DNA coding strand, without other protein factors. $T_4$ and $T_5$ are the shortest Pol Ill termination signals in yeast and mammals, with oligo (dT) terminators longer than T5 being rare in mammals. Accordingly, the multiple polymerase Ill promoter expression constructs of the invention may also include an appropriate oligo (dT) termination signal, i.e., a sequence of 4, 5, 6 or more Ts, operably linked 3' to each RNA Pol Ill promoter cassette in the DNA coding strand. That is, a DNA sequence encoding one or more RNA effector molecules, e.g., a dsRNA hairpin or RNA stem-loop structure to be transcribed, is inserted between the Pol Ill promoter and the termination signal.

The invention provides means for delivering to a host cell sustained amounts of 2, 3, 4, 5, or more different antiviral dsRNA hairpin molecules (e.g., specific for 2, 3, 4, 5, or more different viral sequences or elements), in a genetically stable mode, so as to inhibit viral replication while preventing, decreasing, or delaying generation of viral escape mutants, and without evoking a dsRNA stress response. In accordance with this aspect, each dsRNA hairpin may be expressed from an expression construct, and controlled by e.g. an RNA polymerase Ill promoter. In some such embodiments a single RNA polymerase promoter, e.g. a pol II or pol Ill promoter, may express a plurality of dsRNA hairpins. In some such embodiments the dsRNA hairpins will be present within 5' and 3' flanking miRNA sequences.

Thus, the expression constructs of the invention provide a convenient means for delivering a multi-drug regimen comprising several different RNAs of the invention to a cell or tissue of a host vertebrate organism, thereby potentiating the anti-viral activity, and reducing the likelihood that multiple independent mutational events will produce resistant virus. This provides an important advantage in countering viral variation both within human and animal host populations and temporally within a host due to mutation events.

In certain embodiments, the expression construct contains at least two expression cassettes, each expression cassette directing the expression of a shRNA independently selected from SEQ 10 NOS: 44-81, such as SEQ 10 NOS: 50, 58, 61, and 72. Each expression cassette may independently comprise at least one promoter, e.g., an RNA polymerase Ill promoter selected from a U6 promoter, a 7SK promoter, an H1 promoter, and an MRP promoter. For example, each expression cassette may comprise a 7SK promoter driving the expression of at least one double-stranded RNA effector molecule, and an RNA pol Ill termination signal.

Pharmaceutical Compositions

The RNAs and constructs of the invention may be formulated as pharmaceutical compositions, comprising, in addition to effective amounts of the RNA(s) or construct(s) necessary to produce the desired biological effect, pharmaceutically acceptable carriers. Such carriers may comprise, for example, agents for facilitating the transfection of mammalian cells, which are well known. Exemplary transfection agents and compositions, which may be used in accordance with the present invention, are Lipofectamine2000™ (Invitrogen, Carlsbad, Cal.), as well as those reviewed and described in US 2006/0084617 published Apr. 20, 2006, which is hereby incorporated by reference in its entirety.

See also, the methods and compositions for delivery of nucleic acids as taught in in WO 2006/033756, the teaching of which is hereby incorporated herein in its entirety. Nucleic acids such as shRNAs may also be delivered to distal organs such as the liver by transfecting skeletal muscle cells (e.g., injection, injection/electroporation, or hydrodynamic vessel delivery) with an expression vector as taught in U.S. Ser. No. 11/935,925 (PCT/US2007/83805), the teaching of which is hereby incorporated by reference in its entirely.

In various embodiments, the pharmaceutical composition includes about 1 ng to about 20 mg of nucleic acid, e.g., RNA, DNA, plasmids, viral vectors, recombinant viruses, or mixtures thereof (as described above), which provide the desired amounts of the nucleic acid molecules. In some embodiments, the composition contains about 10 ng to about 10 mg of nucleic acid, about 0.1 mg to about 500 mg, about 1 mg to about 350 mg, about 25 mg to about 250 mg, or about 100 mg of nucleic acid. Those of skill in the art of clinical pharmacology can readily arrive at appropriate dosing schedules with routine experimentation.

Other suitable carriers include, but are not limited to, saline, buffered saline, dextrose, water, glycerol, ethanol, and combinations thereof. The pharmaceutical composition generally contains one or more pharmaceutically acceptable additives suitable for the selected route and mode of administration. These compositions may be administered by, without limitation, any parenteral route including intravenous (IV) or intra-arterial (IA) (including hydrodynamic delivery methods in which increasing intravessel pressure increases transfection of the surrounding cells), intramuscular (IM), intramuscular/electroporation, subcutaneous (SC), intradermal, intraperitoneal, intrathecal, as well as topically, orally, and by mucosal routes of delivery such as intranasal, inhalation, rectal, vaginal, buccal, and sublingual. Generally, the pharmaceutical compositions of the invention are prepared for administration to mammalian subjects including primates and humans, and are in the form of liquids, including sterile, non-pyrogenic liquids for injection, emulsions, powders, aerosols, tablets, capsules, enteric coated tablets, or suppositories.

Methods for Inhibiting Expression of Target Polynucleotides

The invention further provides a method for silencing an HCV RNA in a mammalian cell. As used herein, the term silencing of an HCV RNA refers to reducing the abundance of the target polynucleotide in the cell, or in a patient treated with a sequence-specific anti-HCV agent of the invention, whether via RNA stability and/or via replication rate of the HCV polynucleotide, including inhibitory effects on production, levels or persistence of positive and/or negative strand HCV RNA, including various qualitative and quantitative measures of HCV viral load, e.g., quantitative PCR, transcription-mediated amplification (TMA), and branched DNA assay (bONA). HCV RNA silencing also includes inhibitory effects on viral protein expression. The target polynucleotide (e.g., HCV RNA) may be reduced by about $\frac{1}{2}$, $\frac{1}{5}$, $\frac{1}{10}$, $\frac{1}{100}$ as compared to a positive control cell (e.g., a cell infected with HCV). In some embodiments, the target polynucleotide is undetectable in cells transfected or patients treated with an agent, composition (including pharmaceutical composition), or construct of the invention).

In this aspect, the invention comprises administering to a mammalian cell, such as a primate or human cell infected with HCV, at least one agent, composition, or construct of the invention, as described previously herein, including small-hairpin RNAs and including the encoding expression constructs.

The cell in such embodiments may be a cell culture, or may be an animal model or patient. In these embodiments, the invention provides a method of reducing levels of HCV RNA in a cell either in vitro or in vivo, as well as methods for reducing an HCV titer in vitro or in vivo. In a preferred aspect, the agent is capable of reducing HCV replication in a human hepatocyte in an in vitro HCV infection/replication model such as the recently developed infectious cell culture systems, which more closely reflect actual human HCV infection. The JFH-1 HCV clone, utilized in the Examples below, which is able to replicate efficiently in Huh? cells and can secrete infectious viral particles, represents one such improved model. See e.g., Zhong et al., *Robust hepatitis C virus infection in vitro, PNAS,* 102, No. 26, pp 9294-9299, (2005). See also Yi M, Villanueva R A, Thomas D L, Wakita T, Lemon S M. *Production of infectious eenotype 1a hepatitis C virus (Hutchinson strain) in cultured human hepatoma cells. Proc Natl Acad Sci USA* 2006; 103(7): 2310-2315. In accordance with these embodiments, the double-stranded RNA effector molecules may be introduced into the cell by transforming or transfecting a cell with an expression construct of the invention, or alternatively by directly introducing the double stranded RNA.

The present invention further provides a method for treating, ameliorating or preventing HCV infection in a patient (e.g., a patient having, or at risk of acquiring an HCV infection), comprising administering to said patient, including primates such as humans, an effective amount of an agent, composition, or construct of the invention, suitable for triggering RNAi-mediated degradation of the patient. Thus, the method of the invention reduces viral replication in infected cells, and in certain embodiments, eliminated the infection. The presence of HCV RNA in the blood is considered to be an indication that the virus is actively replicating (reproducing and infecting new cells). In some embodiments, HCV viral load is reduced (by 10%, 20%, 50%, 75%, 90% or more) in an infected individual administered a sequence-specific dsRNA of the invention. In some aspects, viral load will be reduced from high to low levels (less than 2 million copies/ml), desirably to undetectable levels. It is thought that individuals with viral load below 400,000 IU/ml respond better to therapeutic agents that those with higher levels of virus.

The present invention may, in certain embodiments, employ the methods disclosed in U.S. Ser. No. 11/935,925 (PCT/US2007/83805), "In Vivo Delivery of Double Stranded RNA to a Target Cell", which is hereby incorporated by reference in its entirety. Specifically, delivery into skeletal muscle cells of expression constructs encoding dsRNA(s) may result in targeted inhibition of gene expression in other organs and tissues of the body such as liver. The intramuscular delivery may be achieved in a variety of ways, including needle or needleless IM injection, IM injection/electroporation, and intravascular/hydrodynamic delivery. Without being bound by any particular theory, delivery of dsRNA to distal tissues such as liver cells, for example, may be mediated by extracellular vesicles (exovesicles) containing expressed dsRNA or injected siRNA or shRNA that bud from the surface of transfected muscle cells.

The HCV treated by the method of the invention (e.g., targeted by the agents, compositions, and constructs described herein) may be any genotype, subtype, or quasispecies, including genotypes 1a, 1b, 2a, 2b, 3a, 4 and 5, and combinations thereof. In certain embodiments, the HCV infection is non-responsive to interferon-based therapy, and/or other nucleoside analogs such as ribavirin, or other antivirals, making the methods of the invention particularly desirable. In other embodiments, the agents, compositions, and constructs are administered before, during, or after interferon therapy, where necessary to control or eliminate infection.

In certain embodiments, the agents, compositions, and constructs of the invention are administered so as to inhibit viral replication without evoking a dsRNA stress response. Further, unlike traditional antiviral agents, the method of the present invention may reduce the likelihood that multiple independent mutational events will produce resistant virus, thereby providing an important advantage in countering viral variation both within human and animal host populations and temporally within a host due to mutation events.

Some dsRNA sequences, possibly in certain cell types and through certain delivery methods, may result in an interferon response. The methods of the invention may be performed so as not to trigger an interferon/PKR response, for instance by using shorter dsRNA molecules between 20 to 25 base pairs, by expressing dsRNA molecules intracellularly, or by using other methods known in the art. See US Published Application 20040152117, which is herein incorporated by reference. For instance, one of the components of an interferon response is the induction of the interferon-induced protein kinase PKR. To prevent an interferon response, interferon and PKR responses may be silenced in the transfected and target cells using a dsRNA species directed against the mRNAs that encode proteins involved in the response. Alternatively, interferon response promoters are silenced using dsRNA, or the expression of proteins or transcription factors that bind interferon response element (IRE) sequences is abolished using dsRNA or other known techniques.

By "under conditions that inhibit or prevent an interferon response or a dsRNA stress response" is meant conditions that prevent or inhibit one or more interferon responses or cellular RNA stress responses involving cell toxicity, cell death, an anti-proliferative response, or a decreased ability of a dsRNA to carry out a PTGS event. These responses include, but are not limited to, interferon induction (both Type 1 and Type II), induction of one or more interferon stimulated genes, PKR activation, 2'5'-OAS activation, and any downstream cellular and/or organismal sequelae that result from the activation/induction of one or more of these responses. By "organismal sequelae" is meant any effect(s) in a whole animal, organ, or more locally (e.g., at a site of injection) caused by the stress response. Exemplary manifestations include elevated cytokine production, local inflammation, and necrosis. Desirably the conditions that inhibit these responses are such that not more than 95%, 90%, 80%, 75%, 60%, 40%, or 25%, and most desirably not more than 10% of the cells undergo cell toxicity, cell death, or a decreased ability to carry out a PTGS event, compared to a cell not exposed to such interferon response inhibiting conditions, all other conditions being equal (e.g., same cell type, same transformation with the same dsRNA).

Apoptosis, interferon induction, 2'5'-OAS activation/induction, PKR induction/activation, anti-proliferative responses, and cytopathic effects are all indicators for the RNA stress response pathway. Exemplary assays that can be used to measure the induction of an RNA stress response as described herein include a TUNEL assay to detect apoptotic cells, ELISA assays to detect the induction of alpha, beta and gamma interferon, ribosomal RNA fragmentation analysis to detect activation of 2'5'-OAS, measurement of phosphorylated eiF2a as an indicator of PKR (protein kinase RNA inducible) activation, proliferation assays to detect changes in cellular proliferation, and microscopic analysis of cells to identify cellular cytopathic effects. See, e.g., US Published Application 20040152117, which is herein incorporated by reference.

Methods for Making Agents and Compositions

The dsRNA molecules and constructs of the invention may be made using conventional molecular biology techniques, including standard gene cloning and in vitro RNA synthesis protocols. Such methods are well known, and are described in Sambrook et al, *Molecular Cloning: A Laboratory Manual*, 2nd edition, Cold Spring Harbor Laboratory Press (1989); and Ausubel et al., ed. Current Protocols in Molecular Biology, John Wiley & Sons, Inc. (1987)). See also the methods taught in U.S. Pat. No. 6,143,527, "Chain reaction cloning using a bridging oligonucleotide and DNA ligase".

The following examples are provided to describe and illustrate the present invention. As such, they should not be construed to limit the scope of the invention. Those in the art will well appreciate that many other embodiments also fall within the scope of the invention, as it is described hereinabove and in the claims

EXAMPLES

The following Examples are provided for illustration only.

All possible 21-mer and 27-mer expressed shRNAs were constructed based on HCV Conserved Regions 1 (SEQ 10 NO: 2), 2 (SEQ 10 NO: 3) and 5 (SEQ IO NO: 4). Thus, for shRNAs targeting Conserved Region 1, twenty-six 21-mers and sixteen 27-mers were constructed; for Conserved Region 2, thirty-nine 21-mers and thirty-three 27-mers were constructed; and for Conserved Region 5, twenty-eight 21-mers and sixteen 27-mers were constructed.

Example 1

Silencing HCV Replication in a Viral Infection Cell Culture Model

A human liver-derived cell line such as the Huh? cell line is transfected with an eiRNA plasmid expressing short-hairpin RNA (shRNA) molecules that comprise sequences homologous and complementary to the identified conserved sequences in the HCV genome. Following internalization of the plasmid into hepatocytes and nuclear localization, transcription of the eiRNA plasmid from one or more RNA pol III promoters results in production of the HCV-specific shRNAs.

The transfected cells are then infected with HCV JFH-1 virus. The JFH-1 clone is able to replicate efficiently in Huh? cells and can secrete infectious viral particles. See e.g., Zhong et al., *Robust hepatitis C virus infection in vitro, PNAS*, 102, No. 26, pp 9294-9299, (2005).

Using this model, cells were transfected with various eiRNA constructs and then infected with HCV virus. The cells were then monitored for loss of HCV replication as described below.

The following is an example of an experiment that was performed using eiRNA vectors encoding HCV sequences derived from GenBank accession number AB047639. HCV sequences in these described eiRNA vectors were highly conserved sequences identified as described elsewhere herein. The particular eiRNA backbone vector used for this experiment contained a 7SK promoter to drive expression of the encoded RNAs. Each vector encoded only one shRNA. The shRNA coding sequence was followed by an RNA pol III termination sequence. Sequences of the 7SK promoter, RNA pol Ill termination signal, and encoded shRNAs are all shown at the end of the example. Similar vectors containing U6 promoters (another RNA pol Ill type 3 promoter) and RNA pol Ill termination signals are commercially available such as the "silentGene-2 Cloning Systems" vector from Promega, Inc., Madison, Wis. One of ordinary skill in the art can also create them according to the information provided herein.

Experimental Procedure: Transfection.

Huh7 cells cultured in DMEM medium were seeded into 96-well plates at a density of $4 \times 10^3$ cells/well. All transfections were performed the day after cell seeding using Lipofectamine2000™ (Invitrogen, Carlsbad, Cal.) according to the manufacturer's directions. In this experiment, cells were transfected with 200 ng of the eiRNA plasmids and were infected 12 hours later with HCV infectious viral clone JFH-1 at a multiplicity of infection (MOI) of 0.1 ffu/cell. DNA was held constanUtransfection at 200 ng. In experiments where less than 200 ng of the eiRNA plasmid was transfected, the remainder of the DNA is made up by including an inert plasmid DNA, pGL2-Basic (Promega, Madison Wis.) in amounts that brought the total DNA in the transfection to 200 ng. Prior to transfection, medium was removed from the cells and the cells washed with phosphate-buffered saline (PBS), followed by addition of 100 ul of DMEM containing 10% Fetal Bovine Serum (FBS). The DNA/Lipofectamine2000 transfection mix was added to the cells and these were incubated at 3rC for 12 hours. The medium containing the transfection mix was then removed and the cells were washed once with PBS. At this point, 100 ul of DMEM containing 10% FBS was added to the cells. Infection with JFH-1 then commenced with the addition of the virus at a MOI of 0.1 ffu/cell. All transfections were carried out in triplicate. Control groups were pGL2-basic alone (200 ng of pGL2-basic), a green fluorescent protein (GFP) plasmid instead of the eiRNA plasmid (200 ng pGFP), and a group that was untransfected but was infected with JFH-1 at the same MOI.

Monitoring Cells for Loss of HCV Replication.

At 48 hours following transfection, cells were monitored for the loss or reduction in HCV replication by measuring viral RNA by quantitative reverse-transcription PCR (qRT-PCR). The cells were lysed using Total RNA Lysis Buffer (Applied Biosystems, Foster City, Calif.) and the RNA was harvested using an ABI Prism 6100 Nucleic Acid Prep Station (Applied Biosystems). HCV RNA was quantified by qRT-PCR using a SYBR-green labeled probe. The PCR primers used to amplify a 75 bp product corresponding the 5' UTR of the genotype 2a HCV genome (GenBank AB047639) were 5'-TCTGCGGAACCGGTGAGTA-3' (sense) (SEQ ID NO: 82) and 5'-TCAGGCAGTACCACAAGGC-3' (antisense) (SEQ ID NO: 83). The PCR primers used to amplify a 225 bp product of the human GAPDH coding sequence (GenBank NM002046) were 5'-GAAGGTGAAGGTCGGAGTC-3' (sense) (SEQ ID NO: 84) and 5'-GAAGATGGTGATGG-GATTTC-3' (antisense) (SEQ ID NO: 85). HCV and GAPDH transcript levels were determined relative to a standard curve comprised of serial dilutions of plasmid containing the HCV eDNA or the human GAPDH gene. HCV copies per ug of total cellular RNA were normalized to GAPDH transcript levels using a modified comparative threshold cycle method ddCt (Z (ddCtl); where ddCt is the difference between the Average GAPDH and the GAPDH of the individual sample. Fold reduction in HCV copy numbers was calculated as: (average number of HCV copies per ug total cellular RNA in control transfected samples)+(average number of HCV copies per ug total cellular RNA in eiRNA transfected samples).

Results:

A number of the shRNA plasmids transfected led to a decrease in HCV replication as compared to negative controls. The results in Table 1 are presented as the average of three plates and are shown as both fold-inhibition and the equivalent percent reduction.

A total of 135 eiRNAs (plasmid expressed shRNAs) containing 21-mer double-stranded stem sequences and 118 eiRNAs containing 27-mer double-stranded stem sequences were tested in the assay. The eiRNAs showing a 4-fold or greater inhibition are listed in Table 1 along with a representative selection of eiRNAs showing less than 4-fold inhibition. The eiRNA vectors encode the HCV sequences listed in Table 2. The sequences of the shRNAs are shown as well as the map coordinates of the sense sequence (found 3' to the underlined 9 nt loop sequence) relative to the HCV JFH-1 clone, GenBank accession number AB047639 (SEQ ID NO: 1). The sequences of the encoded shRNAs include an antisense HCV sequence followed by the loop sequence (underlined in Table 1) followed by a second HCV sequence, which is the complement to the first HCV sequence. (It will be understood that either the antisense or sense sequence may be located 5' to the loop sequence, i.e., 5'-antisense-loop-sense-3' or 5'-sense-loop-antisense-3'.) The loop structure does not need to be a fixed sequence or length, and several loop sequences were used with no significant impact on the functioning of the eiRNA construct. The second HCV sequence is followed by a series of residues, e.g., 1, 2, 3, or more Ts, preferably at least 4 or 5 Ts, that function as the termination signal for RNA pol Ill. These T nucleotides are not included in Table 2. Table 2 recites SEQ ID NOs: 44-81 in order of appearance.

TABLE 1

| eiRNA | Fold inhibition | Percent reduction |
|---|---|---|
| HCV 5' 21-2 | 1 | 0 |
| HCV 5' 21-16 | 1 | 0 |
| HCV 5' 21-50 | 1 | 0 |
| HCV 5'-21-55 | 5 | 80 |
| HCV 5'-21-56 | 5 | 80 |
| HCV 5'-21-57 | 5 | 80 |
| HCV 5' 21-61 | 7 | 85.7 |
| HCV 5' 21-63 | 4 | 75 |
| HCV 5' 21-70 | 1 | 0 |
| HCV 5' 21-73 | 1 | 0 |
| HCV 5' 21-88 | 5 | 80 |
| HCV 5' 21-89 | 5 | 80 |
| HCV 5' 21-90 | 4 | 75 |
| HCV 5' 21-92 | 7 | 85.7 |
| HCV 5' 21-94 | 9 | 88.9 |
| HCV 5'-21-122 | 4 | 75 |
| HCV 5'-21-123 | 4 | 75 |
| HCV 5'-21-124 | 7 | 85.7 |
| HCV 5'-21-125 | 5 | 80 |
| HCV 5'-21-126 | 8 | 87.5 |
| HCV 5'-21-127 | 7 | 85.7 |
| HCV 5'-21-128 | 8 | 87.5 |
| HCV 5'-21-129 | 4 | 75 |
| HCV 5'-21-130 | 6 | 83.3 |
| HCV 5'-21-131 | 3 | 67 |
| HCV 5'-21-133 | 12 | 91.7 |
| HCV 5'-21-134 | 9 | 88.9 |
| HCV 5'-21-135 | 10 | 90 |
| HCV 5' 27-1 | 1 | 0 |
| HCV 5' 27-8 | 4 | 75 |
| HCV 5' 27-9 | 4 | 75 |
| HCV 5' 27-12 | 1 | 0 |
| HCV 5' 27-16 | 8 | 87.5 |
| HCV 5' 27-45 | 1 | 0 |
| HCV 5' 27-53 | 4 | 75 |
| HCV 5' 27-73 | 1 | 0 |
| HCV 5' 27-111 | 1 | 0 |

| Sequence (5' antisense-loop-sense 3') | nucleotide coordinates sense sequence relative GenBank No. AB047639 |
|---|---|
| TAGTTCCTCACAGGGGAGTGAagagaacttTCACTCCCCTGTGAGGAACTA | 36-56 |
| CCGGTTCCGCAGACCACTATGagagaacttCATAGTGGTCTGCGGAACCGG | 50-70 |
| TATGGCTCTCCCGGGAGGGGagagaacttCCCCCTCCCGGGAGAGCCATA | 121-141 |
| ACCACTATGGCTCTCCCGGGAagagaacttTCCCGGGAGAGCCATAGTGGT | 126-146 |
| GACCACTATGGCTCTCCCGGGagagaacttCCCGGGAGAGCCATAGTGGTC | 127-147 |
| AGACCACTATGGCTCTCCCGGagagaacttCCGGGAGAGCCATAGTGGTCT | 128-148 |
| CCGCAGACCACTATGGCTCTCagagaacttGAGAGCCATAGTGGTCTGCGG | 132-152 |
| TTCCGCAGACCACTATGGCTCagagaacttGAGCCATAGTGGTCTGCGGAA | 134-154 |
| TCACCGGTTCCGCAGACCACTagagaacttAGTGGTCTGCGGAACCGGTGA | 141-161 |
| TACTCACCGGTTCCGCAGACCagagaacttGGTCTGCGGAACCGGTGAGTA | 144-164 |
| GCAGTACCACAAGGCCTTTCGagagaacttCGAAAGGCCTTGTGGTACTGC | 271-291 |
| GGCAGTACCACAAGGCCTTTCagagaacttGAAAGGCCTTGTGGTACTGCC | 272-292 |
| AGGCAGTACCACAAGGCCTTTagagaacttAAAGGCCTTGTGGTACTGCCT | 274-294 |
| TCAGGCAGTACCACAAGGCCTagagaacttAGGCCTTGTGGTACTGCCTGA | 275-295 |
| TATCAGGCAGTACCACAAGGCagagaacttGCCTTGTGGTACTGCCTGATA | 277-297 |
| AGACCTCCCGGGGCACTCGCAagagaacttTGCGAGTGCCCCGGGAGGTCT | 305-325 |
| GAGACCTCCCGGGGCACTCGCagagaacttGCGAGTGCCCCGGGAGGTCTC | 306-326 |
| CGAGACCTCCCGGGGCACTCGagagaacttCGAGTGCCCCGGGAGGTCTCG | 307-327 |
| ACGAGACCTCCCGGGGCACTCagagaacttGAGTGCCCCGGGAGGTCTCGT | 308-328 |
| TACGAGACCTCCCGGGGCACTagagaacttAGTGCCCCGGGAGGTCTCGTA | 309-329 |
| CTACGAGACCTCCCGGGGCACagagaacttGTGCCCCGGGAGGTCTCGTAG | 310-330 |
| TCTACGAGACCTCCCGGGGCAagagaacttTGCCCCGGGAGGTCTCGTAGA | 311-331 |
| GTCTACGAGACCTCCCGGGGCagagacttGCCCCGGGAGGTCTCGTAGAC | 312-332 |
| GGTCTACGAGACCTCCCGGGGagagaacttCCCCGGGAGGTCTCGTAGACC | 313-333 |
| CGGTCTACGAGACCTCCCGGGagagaacttCCCGGGAGGTCTCGTAGACCG | 314-334 |
| ACGGTCTACGAGACCTCCCGGagagaacttCCGGGAGGTCTCGTAGACCGT | 315-335 |

-continued

| Sequence (5' antisense-loop-sense 3') | nucleotide coordinates sense sequence relative GenBank No. AB047639 |
|---|---|
| CACGGTCTACGAGACCTCCCGagagaacttCGGGAGGTCTCGTAGACCGTG | 316-336 |
| GCACGGTCTACGAGACCTCCCagagaacttGGGAGGTCTCGTAGACCGTGC | 317-337 |
| TGCACGGTCTACGAGACCTCCagagaacttGGAGGTCTCGTAGACCGTGCA | 318-338 |
| GACAGTAGTTCCTCACAGGGGAGTGATagagaacttATCACTCCCCTGTGAGGAACTACTGTC | 35-61 |
| GCGTGAAGACAGTAGTTCCTCACAGGGagagaacttCCCTGTGAGGAACTACTGTCTTCACGC | 42-68 |
| TGCGTGAAGACAGTAGTTCCTCACAGGagagaacttCCTGTGAGGAACTACTGTCTTCACGCA | 43-69 |
| TTCTGCGTGAAGACAGTAGTTCCTCACagagaacttGTGAGGAACTACTGTCTTCACGCAGAA | 46-72 |
| CGCTTTCTGCGTGAAGACAGTAGTTCCagagaacttGGAACTACTGTCTTCACGCAGAAAGCG | 50-76 |
| GACCACTATGGCTCTCCCGGGAGGGGGagagaacttCCCCCTCCCGGGAGAGCCATAGTGGTC | 122-148 |
| GTTCCGCAGACCACTATGGCTCTCCCGagagaacttCGGGAGAGCCATAGTGGTCTGCGGAAC | 129-155 |
| CAATTCCGGTGTACTCACCGGTTCCGCagagaacttGCGGAACCGGTGAGTACACCGGAATTG | 149-175 |
| TCTACGAGACCTCCCGGGGCACTCGCAagagaacttTGCGAGTGCCCCGGGAGGTCTCGTAGA | 305-331 |

TABLE 3

| eiRNA | Sense sequence |
|---|---|
| HCV5'-21-2 (SEQ ID NO: 5) | tcactcccctgtgaggaacta |
| HCV5'-21-16 (SEQ ID NO: 6) | ggaactactgtcttcacgcag |
| HCV5'-21-50 (SEQ ID NO: 7) | cccctcccgggagagccata |
| HCV5'-21-55 (SEQ ID NO: 8) | tcccgggagagccatagtggt |
| HCV5'-21-56 (SEQ ID NO: 9) | cccgggagagccatagtggtc |
| HCV5'-21-57 (SEQ ID NO: 10) | ccgggagagccatagtggtct |
| HCV5'-21-61 (SEQ ID NO: 11) | gagagccatagtggtctgcgg |
| HCV5'-21-63 (SEQ ID NO: 12) | gagccatagtggtctgcggaa |
| HCV5'-21-70 (SEQ ID NO: 13) | agtggtctgcggaaccggtga |
| HCV5'-21-73 (SEQ ID NO: 14) | ggtctgcggaaccggtgagta |
| HCV5'-21-88 (SEQ ID NO: 15) | cgaaaggccttgtggtactgc |
| HCV5'-21-89 (SEQ ID NO: 16) | gaaaggccttgtggtactgcc |
| HCV5'-21-90 (SEQ ID NO: 17) | aaaggccttgtggtactgcct |
| HCV5'-21-92 (SEQ ID NO: 18) | aggccttgtggtactgcctga |
| HCV5'-21-94 (SEQ ID NO: 19) | gccttgtggtactgcctgata |

TABLE 3-continued

| eiRNA | Sense sequence |
|---|---|
| HCV5'-21-122 (SEQ ID NO: 20) | tgcgagtgccccgggaggtct |
| HCV5'-21-123 (SEQ ID NO: 21) | gcgagtgccccgggaggtctc |
| HCV5'-21-124 (SEQ ID NO: 22) | cgagtgccccgggaggtctcg |
| HCV5'-21-125 (SEQ ID NO: 23) | gagtgccccgggaggtctcgt |
| HCV5'-21-126 (SEQ ID NO: 24) | agtgccccgggaggtctcgta |
| HCV5'-21-127 (SEQ ID NO: 25) | gtgccccgggaggtctcgtag |
| HCV5'-21-128 (SEQ ID NO: 26) | tgccccgggaggtctcgtaga |
| HCV5'-21-129 (SEQ ID NO: 27) | gccccgggaggtctcgtagac |
| HCV5'-21-130 (SEQ ID NO: 28) | ccccgggaggtctcgtagacc |
| HCV5'-21-131 (SEQ ID NO: 29) | cccgggaggtctcgtagaccg |
| HCV5'-21-132 (SEQ ID NO: 30) | ccgggaggtctcgtagaccgt |
| HCV5'-21-133 (SEQ ID NO: 31) | cgggaggtctcgtagaccgtg |
| HCV5'-21-134 (SEQ ID NO: 32) | gggaggtctcgtagaccgtgc |
| HCV5'-21-135 (SEQ ID NO: 33) | ggaggtctcgtagaccgtgca |

TABLE 3-continued

| eiRNA | Sense sequence |
|---|---|
| HCV5'-27-1 (SEQ ID NO: 34) | atcactccctgtgaggaactactgtc |
| HCV5'-27-8 (SEQ ID NO 35) | ccctgtgaggaactactgtcttcacgc |
| HCV5'-27-9 (SEQ ID NO: 36) | cctgtgaggaactactgtcttcacgca |
| HCV5'-27-12 (SEQ ID NO: 37) | gtgaggaactactgtcttcacgcagaa |
| HCV5'-27-16 (SEQ ID NO: 38) | ggaactactgtcttcacgcagaaagcg |
| HCV5'-27-45 (SEQ ID NO: 39) | cccctcccgggagagccatagtggtc |
| HCV5'-27-53 (SEQ ID NO: 40) | cgggagagccatagtggtctgcggaac |
| HCV5'-27-73 (SEQ ID NO: 41) | gcggaaccggtgagtacaccggaattg |
| HCV5'-27-111 (SEQ ID NO: 42) | tgcgagtgccccgggaggtctcgtaga |

Preferred for use in anti-HCV dsRNA effector molecules of the invention are the following conserved and actively inhibitory HCV sequences:
HCV-5-21-56, SEQ ID NO: 9, and its complement, which may be utilized as a duplex dsRNA, or as an shRNA, such as that of SEQ. ID. NO: 48;
HCV-5-21-61, SEQ. ID NO: 11, and its complement, which may be utilized as a duplex dsRNA, or as an shRNA, such as that of SEQ. ID NO: 50;
HCV-5-21-90, SEQ. ID NO: 17, and its complement, which may be utilized as a duplex dsRNA, or as an shRNA, such as that of SEQ. ID NO: 56;
HCV-5-21-94, SEQ. ID NO: 19, and its complement, which may be utilized as a duplex dsRNA, or as an shRNA, such as that of SEQ. ID NO: 58;
HCV-5-21-124, SEQ. ID NO:22, and its complement, which may be utilized as a duplex dsRNA, or as an shRNA, such as that of SEQ. ID NO: 61;
HCV-5-21-128, SEQ. ID NO: 26, and its complement, which may be utilized as a duplex dsRNA, or as an shRNA, such as that of SEQ. ID NO: 65;
HCV-5-21-133, SEQ. ID NO:31, and its complement, which may be utilized as a duplex dsRNA, or as an shRNA, such as that of SEQ. ID NO:70;
HCV-5-21-134, SEQ. ID NO: 32, and its complement, which may be utilized as a duplex dsRNA, or as an shRNA, such as that of SEQ. ID NO:71;
HCV-5-21-135, SEQ. ID NO:33, and its complement, which may be utilized as a duplex dsRNA, or as an shRNA, such as that of SEQ. ID NO:72;
In preferred embodiments, two, three, four, five or more of the above-identified anti-HCV dsRNA effector molecules are administered concomitantly to a human cell infected with HCV. In some aspects, an expression construct or constructs encoding such a plurality of dsRNA effector molecules is/are administered concomitantly to a human cell infected with HCV. In some aspects said two or more dsRNA effector molecules will comprise in double-stranded conformation two or more sequences selected from SEQ ID NOS: 9, 11, 17, 19, 22, 26, 31, 32, and 33. In some aspects said two or more dsRNA effector molecules will comprise two or more sequences selected from SEQ ID NOS: 48, 50, 56, 58, 61, 65, 70, 71, and 72.

The actively inhibitory HCV sequences map to four conserved and highly active target regions (ATR) (see FIG. 1):
ATR-1: 5'-CCCTGTGAGGAACTACTGTCTTCACGCA-GAA-3' (SEQ ID NO: 86), mapping to nucleotide coordinates 42 to 76 of GenBank Accession No. AB047639, found within Conserved Region 1 (SEQ ID NO: 2).
ATR-2: 5'-TCCCGGGAGAGCCATAGTGGTCTGCG-GAA-3' (SEQ ID NO: 87), mapping to nucleotide coordinates 126 to 154 of GenBank Accession No. AB047639, found within Conserved Region 2 (SEQ ID NO: 3).
ATR-3: 5'-CGAAAGGCCTTGTGGTACTGC-3' (SEQ ID NO: 88), mapping to nucleotide coordinates 271 to 297 of GenBank Accession No. AB047639, found within Conserved Region 5 (SEQ ID NO: 4).
ATR-4: 5'-TGCGAGTGCCCCGGGAGGTCTCGTAGAC-CGTGCA3' (SEQ ID NO: 89), mapping to nucleotide coordinates 305 to 338 of GenBank Accession No. AB047639, found within Conserved Region 5 (SEQ ID NO: 4).

Example 2

Silencing HCV Replication Using a Plasmid Expressing Multiple eiRNA Molecules

Plasmids expressing multiple eiRNAs (shRNAs) (known as multi-cistronic plasmids) can be used to inhibit HCV replication in a cell culture model (as described in Example 1). In this example, sequences encoding four different shRNA molecules were sequentially cloned into a single plasmid expression vector, each operably linked to an individual RNA polymerase III promoter and terminator. Each shRNA contained a different sequence homologous and complementary to the HCV genome that was previously shown to inhibit HCV replication. By expressing several different dsRNA molecules within an HCV infected cell or a human cell capable of HCV infection, the eiRNA expression vector represents a multi-drug regimen having an enhanced ability to inhibit HCV replication and to prevent the development during therapy of HCV escape mutants.

Figure 2:
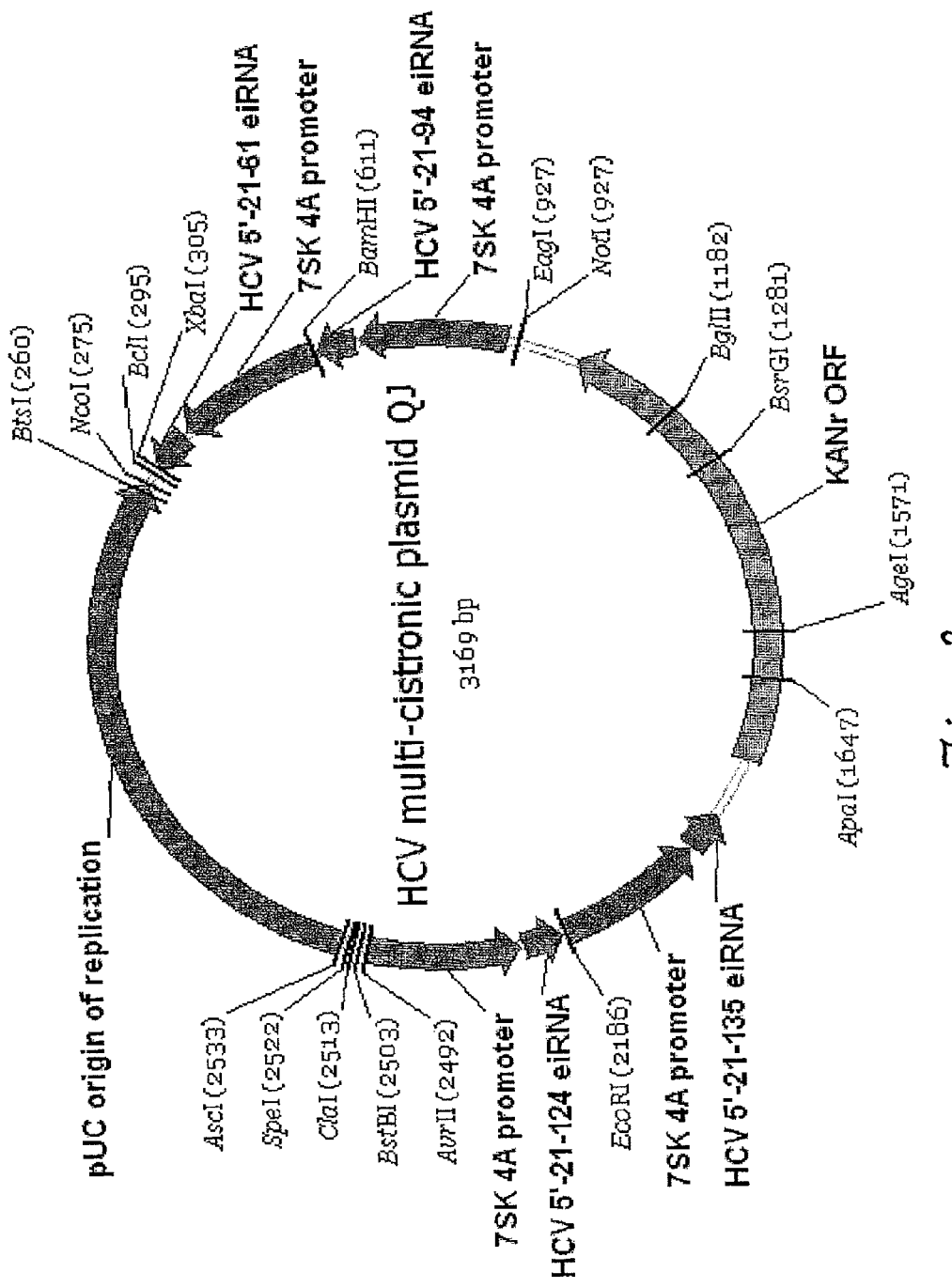
FIG. 2 is a plasmid diagram of the multi-cistronic plasmid QJ, which expresses four different active shRNAs, HCV 5'-21-61, HCV 5'-21-94, HCV 5'-21-124, and HCV 5'-21-135.

We cloned the genes for four HCV-suppressive shRNAs into a single plasmid, each operably linked to a different RNA polymerase III promoter and terminator. The four shRNAs were 1) shRNA SEQ ID NO: 50, which includes HCV 5'-21-61 (SEQ ID NO: 11) and its complement; 2) shRNA SEQ ID NO: 58, which includes HCV-5'-21-94 (SEQ. ID NO: 19) and its complement; 3) shRNA SEQ. ID NO: 61, which includes HCV 5'-21-124 (SEQ. ID NO: 22) and its complement; and 4) shRNA SEQ. ID NO: 72, which includes HCV 5'21-135 (SEQ. ID NO: 33) and its complement. (See HCV multi-cistronic plasmid HCV-QJ, FIG. 2). Each shRNA sequence was expressed from a different copy of the RNA pol III promoter 7SK 4A, although one or more other RNA pol III type 3 promoters such as 7SK, H1 and/or U6 could also be used. It may be desirable in some circumstances to select two, three, four or more different promoters to express two, three, four or more different dsRNAs of the invention. The quad-cistron plasmid was constructed essentially as described in WO 2006/0033756 and the 7SK 4A promoter utilized is also described therein. The eiRNAs were transcribed following intracellular uptake of the plasmid.

In the same manner as HCV-QJ (described above), other multi-cistronic plasmids (e.g., including quad-cistron plasmids HVC-QF, HCV-QG, HCV-QH, and HCV-QK), were constructed using different combinations of eiRNAs (anti- HCV shRNAs described herein) that had each been shown to be suppressive of HCV replication in their original mono-cistronic forms (see Table 4 below).

Figure 3:
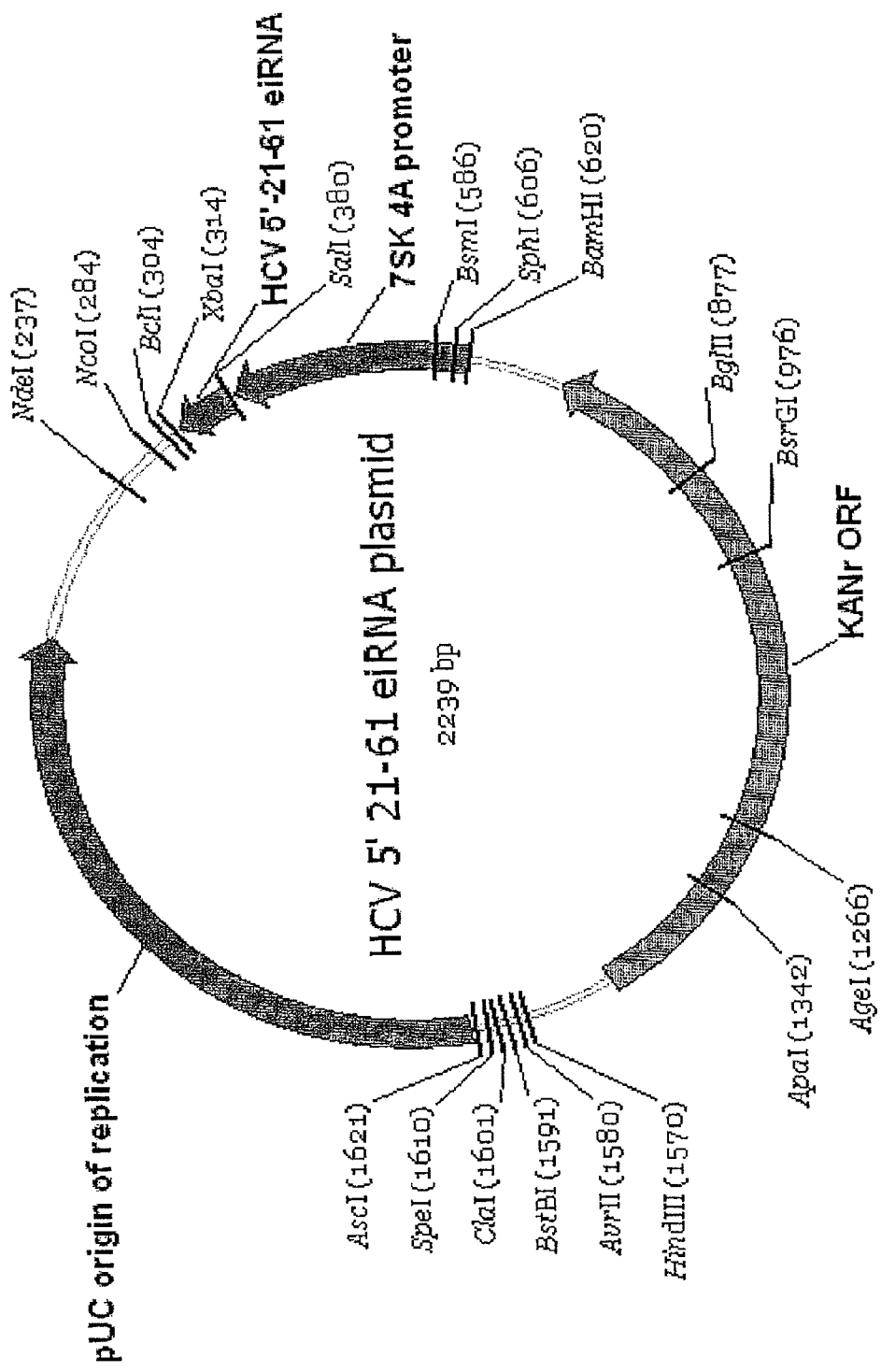
FIG. 3 is a plasmid diagram of a mono-cistronic plasmid HCV 5' 21-61, which expresses the shRNA HCV 5' 21-61 from the 7SK 4A promoter.

Such a mono-cistronic HCV eiRNA expression plasmid (HCV 5'21-61 eiRNA plasmid, which expresses shRNA SEQ ID NO: 50, which includes HCV 5'-21-61 (SEQ ID NO: 11) and its complement) is illustrated in FIG. 3.

Note that any number of combinations, e.g., two, three, four, five or more different suppressive eiRNAs, can constitute the multi-cistronic eiRNA plasmids of the invention. While a combination of two, three, four or more of such different dsRNA effector molecules (e.g., duplex and/or hairpin dsRNAs) may be administered concomitantly to a mammalian cell as a "cocktail" of exogenously generated RNAs, it is desirable in some aspects to express them within a target mammalian cell from a multi-cistronic plasmid as described herein.

TABLE 4

| Multi-cistronic plasmid | shRNA sequence and corresponding HCV sequence |
|---|---|
| HCV-QF | HCV 5' 21-56 (SED. ID. NO: 9) and its complement, expressed as shRNA SEQ ID NO: 48 |
| | HCV 5' 21-135 (SEQ. ID NO: 33) and its complement, expressed as shRNA SEQ. ID NO: 72 |
| | HCV 5' 21-133 (SEQ. ID NO: 31) and its complement, expressed as shRNA SEQ. ID NO: 70 |
| | HCV 5' 21-61 (SEQ. ID NO: 11) and its complement, expressed as shRNA SEQ. ID NO: 50 |
| HCV-QG | HCV-5-21-94 (SEQ. ID NO: 19) and its complement, expressed as shRNA SEQ. ID NO: 58 |
| | HCV 5' 21-135 (SEQ. ID NO: 33) and its complement, expressed as shRNA SEQ. ID NO: 72 |
| | HCV 5' 21-133 (SEQ. ID NO: 31) and its complement, expressed as shRNA SEQ. ID NO: 70 |
| | HCV 5' 21-61 (SEQ. ID NO: 11) and its complement, expressed as shRNA SEQ. ID NO: 50 |
| HCV-QH | HCV-5-21-94 (SEQ. ID NO: 19) and its complement, expressed as shRNA SEQ. ID NO: 58 |
| | HCV-5-21-134 (SEQ. ID NO: 32) and its complement, expressed as shRNA SEQ. ID NO: 71 |
| | HCV-5-21-124 (SEQ. ID NO: 22) and its complement, expressed as shRNA, SEQ. ID NO: 61 |
| | HCV 5' 21-135 (SEQ. ID NO: 33) and its complement, expressed as shRNA SEQ. ID NO: 72 |
| HCV-QJ | HCV-5-21-94 (SEQ. ID NO: 19) and its complement, expressed as shRNA SEQ. ID NO: 58 |
| | HCV 5' 21-61 (SEQ. ID NO: 11) and its complement, expressed as shRNA SEQ. ID NO: 50 |
| | HCV-5-21-124 (SEQ. ID NO: 22) and its complement, expressed as shRNA, SEQ. ID NO: 61 |
| | HCV 5' 21-135 (SEQ. ID NO: 33) and its complement, expressed as shRNA SEQ. ID NO: 72 |
| HCV-QK | HCV-5-21-128 (SEQ. ID NO: 26) and its complement, expressed as shRNA SEQ. ID NO: 65 |
| | HCV-5-21-134 (SEQ. ID NO: 32) and its complement, expressed as shRNA SEQ. ID NO: 71 |
| | HCV 5' 21-133 (SEQ. ID NO: 31) and its complement, expressed as shRNA SEQ. ID NO: 70 |
| | HCV 5' 21-135 (SEQ. ID NO: 33) and its complement, expressed as shRNA SEQ. ID NO: 72 |

The methods that were utilized for transfection of the multi-cistronic plasmids into Huh7 cells, the subsequent infection of these cells with HCV and the quantification of HCV mRNA (as a measure of the suppression of HCV replication) were carried out as described in Example 1 above.

Results.

The suppressive activities that were observed for each of the multi-cistronic plasmids are shown in Table 5. Not only did the use of multiple different dsRNA effector molecules produce a very high level of inhibition of HCV replication, we expect that use of such combinations of different sequence-specific inhibitors will have enhanced ability to prevent the development of HCV escape mutants during therapy.

TABLE 5

| Multi-cistronic plasmid | Fold-inhibition | Percent reduction |
|---|---|---|
| HCV-QF | 12 | 91.7 |
| HCV-QG | 11 | 90.9 |
| HCV-QH | 20 | 95 |
| HCV-QJ | 28 | 96.4 |
| HCV-QK | 25 | 96 |

All publications, patents and patent applications discussed herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method for silencing an hepatitis C virus (HCV) RNA in a mammalian cell comprising administering to said cell at least four double-stranded RNA effector molecules or complexes, comprising: (a) (1) a sequences of at least 19 consecutive nucleotides having at least 90% identity with a nucleotide sequence of SEQ ID NO: 19, SEQ ID NO: 32, SEQ ID NO: 22, and SEQ ID NO: 33; and (2) their complementary sequences; or (b) (1) sequences of at least 19 nucleotides having at least 90% identity with a nucleotide sequence of SEQ ID NO: 19, SEQ ID NO: 11, SEQ ID NO: 22, and SEQ ID NO: 33; and (2) their complementary sequences.

2. The method of claim 1, wherein the double-stranded RNA effector molecules or complexes comprise a double-stranded region of from 19 to 30 base pairs.

3. The method of claim 2, wherein the sequence of at least 19 nucleotides and its complementary sequence are connected via a loop sequence.

4. The method of claim 1, wherein said administering is accomplished by providing to the mammalian cell at least one expression construct capable of expressing the double-stranded RNA effector molecule(s).

5. The method of claim 1, wherein the mammalian cell is a human cell.

6. A method of treating hepatitis C virus (HCV) infection in a patient, comprising administering to said patient an effective amount of an agent for silencing HCV RNA, comprising at least four double stranded RNA effector molecules or complexes that comprise, or a construct that expresses: (a) (1) sequences of at least 19 nucleotides having at least 90% identity with a nucleotide sequence of SEQ ID NO: 19, SEQ ID NO: 31, SEQ ID NO: 22, and SEQ ID NO: 33; and (2) their complementary sequences; or (b) (1) sequences of at least 19 nucleotides having at least 90% identity with a nucleotide sequence of SEQ ID NO: 19, SEQ ID NO: 11, SEQ ID NO: 22, and SEQ ID NO: 33; and (2) their complementary sequences.

7. The method of claim 6, wherein at least one double-stranded RNA effector molecule has a sequence selected from SEQ ID NOs: 50, 58, 61, 71, and 72.

* * * * *